(12) United States Patent
Tipirneni et al.

(10) Patent No.: US 9,060,809 B2
(45) Date of Patent: Jun. 23, 2015

(54) LAGWIRE SYSTEM AND METHOD FOR THE FIXATION OF BONE FRACTURES

(75) Inventors: Kishore Tipirneni, Glendale, AZ (US); Wayne Vassello, Lake Worth, FL (US)

(73) Assignee: ORTHOIP, LLC, Boca Raton, FL (US)

( * ) Notice: Subject to any disclaimer, the term of this patent is extended or adjusted under 35 U.S.C. 154(b) by 4 days.

(21) Appl. No.: 13/118,871

(22) Filed: May 31, 2011

(65) Prior Publication Data

US 2011/0295252 A1 Dec. 1, 2011

Related U.S. Application Data

(63) Continuation-in-part of application No. 12/898,975, filed on Oct. 6, 2010, now abandoned, which is a continuation-in-part of application No. 12/860,122, filed on Aug. 20, 2010, now abandoned, which is a continuation-in-part of application No. 12/491,132, (Continued)

(51) Int. Cl.
*A61B 17/84* (2006.01)
*A61B 17/68* (2006.01)
*A61B 17/70* (2006.01)
*A61B 17/88* (2006.01)
*A61B 17/92* (2006.01)
*A61B 17/62* (2006.01)

(Continued)

(52) U.S. Cl.
CPC ............ *A61B 17/683* (2013.01); *A61B 17/842* (2013.01); *A61B 17/62* (2013.01); *A61B 17/685* (2013.01); *A61B 17/7053* (2013.01); *A61B 17/746* (2013.01); *A61B 17/8605* (2013.01); *A61B 17/861* (2013.01); *A61B 17/8625*

(2013.01); *A61B 17/864* (2013.01); *A61B 17/8685* (2013.01); *A61B 17/8863* (2013.01); *A61B 17/8869* (2013.01); *A61B 17/888* (2013.01); *A61B 17/92* (2013.01)

(58) Field of Classification Search
CPC ........... A61B 17/7053; A61B 17/8685; A61B 217/681; A61B 17/842
USPC ...................... 606/300–321, 62–68; 472/195; 442/352, 195; 267/290
See application file for complete search history.

(56) References Cited

U.S. PATENT DOCUMENTS 200,860 A * 3/1878 French ......................... 267/290
1,025,008 A 4/1912 Miner (Continued)

FOREIGN PATENT DOCUMENTS

FR 2784019 4/2000
GB 2136688 9/1984

(Continued)

OTHER PUBLICATIONS

Final Office Action dated Dec. 7, 2011 in U.S. Appl. No. 12/235,405.

(Continued)

*Primary Examiner* — Matthew Lawson
*Assistant Examiner* — Zade Coley
(74) *Attorney, Agent, or Firm* — Snell & Wilmer L.L.P.

(57) ABSTRACT

A lagwire system and method for facilitating the fixation of bone fractures is disclosed. The lagwire system includes an anchor component, a wire, a sleeve and a cap. The sleeve and cap are operable to slide along the length of the wire and also operable to be used to fixate a fracture individually by using a canal prepared by the anchor and wire.

14 Claims, 31 Drawing Sheets

Related U.S. Application Data filed on Jun. 24, 2009, now abandoned, which is a continuation-in-part of application No. 12/265,890, filed on Nov. 6, 2008, now abandoned, which is a continuation-in-part of application No. 12/235,405, filed on Sep. 22, 2008, now abandoned, which is a continuation-in-part of application No. 11/952,715, filed on Dec. 7, 2007, now Pat. No. 8,828,067, which is a continuation-in-part of application No. 11/742,457, filed on Apr. 30, 2007, now Pat. No. 8,702,768, which is a continuation-in-part of application No. 11/678,473, filed on Feb. 23, 2007, now Pat. No. 8,679,167, which is a continuation-in-part of application No. 10/779,892, filed on Feb. 17, 2004, now Pat. No. 7,591,823, which is a continuation-in-part of application No. 10/272,773, filed on Oct. 17, 2002, now Pat. No. 6,736,819.

(60) Provisional application No. 60/330,187, filed on Oct. 18, 2001.

(51) Int. Cl.
 *A61B 17/74* (2006.01)
 *A61B 17/86* (2006.01)

(56) References Cited

U.S. PATENT DOCUMENTS

| | | |
|---|---|---|
| 2,077,804 A | 4/1937 | Morrision |
| 2,086,321 A * | 7/1937 | Kudo ................ 267/204 |
| 2,381,050 A | 8/1945 | Hardinge |
| 2,397,545 A | 4/1946 | Hardinge |
| 2,414,882 A | 1/1947 | Longfellow |
| 2,490,364 A | 12/1949 | Livingston |
| 2,511,051 A | 6/1950 | Dzus |
| 2,586,556 A * | 2/1952 | Mullikin ................ 411/339 |
| 2,952,254 A * | 9/1960 | Keating ................ 606/67 |
| 3,051,169 A | 8/1962 | Gustaf-Bertil |
| 3,066,274 A * | 11/1962 | Ellis, Jr. ................ 439/391 |
| 3,433,220 A | 3/1969 | Zickel |
| 3,489,143 A | 1/1970 | Halloran |
| 3,606,656 A * | 9/1971 | Kumagai et al. ................ 28/168 |
| 4,035,577 A * | 7/1977 | Loeber ................ 174/84 C |
| 4,112,708 A * | 9/1978 | Fukuda ................ 464/7 |
| 4,147,397 A * | 4/1979 | Iantorno ................ 439/75 |
| 4,341,206 A | 7/1982 | Perrett et al. |
| 4,432,358 A | 2/1984 | Fixel |
| 4,456,005 A * | 6/1984 | Lichty ................ 606/60 |
| 4,617,922 A | 10/1986 | Griggs |
| 4,621,629 A | 11/1986 | Koeneman |
| 4,632,100 A | 12/1986 | Somers et al. |
| 4,640,271 A | 2/1987 | Lower |
| 4,688,561 A | 8/1987 | Reese |
| 4,708,132 A | 11/1987 | Silvestrini |
| 4,741,330 A | 5/1988 | Hayhurst |
| 4,773,406 A | 9/1988 | Spector et al. |
| 4,854,797 A * | 8/1989 | Gourd ................ 411/383 |
| 4,858,601 A | 8/1989 | Glisson |
| 4,863,383 A | 9/1989 | Grafelmann |
| 4,889,110 A | 12/1989 | Galline et al. |
| 4,905,680 A | 3/1990 | Tunc |
| 4,934,935 A | 6/1990 | Edwards |
| 4,940,467 A | 7/1990 | Tronzo |
| 4,959,064 A | 9/1990 | Engelhardt |
| 5,019,079 A | 5/1991 | Ross |
| 5,041,116 A | 8/1991 | Wilson |
| 5,061,137 A * | 10/1991 | Gourd ................ 411/510 |
| 5,088,123 A * | 2/1992 | MacDonald ................ 2/162 |
| 5,100,405 A | 3/1992 | McLaren |
| 5,102,276 A | 4/1992 | Gourd |
| 5,116,336 A | 5/1992 | Frigg |
| 5,116,340 A | 5/1992 | Songer et al. |
| 5,122,133 A | 6/1992 | Evans |
| 5,127,914 A | 7/1992 | Calderale et al. |
| 5,129,901 A | 7/1992 | Decoste |
| 5,141,520 A | 8/1992 | Goble et al. |
| 5,207,753 A | 5/1993 | Badrinath |
| 5,217,462 A | 6/1993 | Asnis et al. |
| 5,269,784 A | 12/1993 | Mast |
| 5,271,543 A * | 12/1993 | Grant et al. ................ 227/179.1 |
| 5,300,075 A | 4/1994 | Gordon |
| 5,306,290 A | 4/1994 | Martins et al. |
| 5,324,292 A | 6/1994 | Meyers |
| 5,336,028 A | 8/1994 | Yamamoto |
| 5,338,139 A | 8/1994 | Swanstrom |
| 5,364,398 A | 11/1994 | Chapman et al. |
| 5,368,605 A | 11/1994 | Miller |
| 5,382,124 A | 1/1995 | Frattarola |
| 5,405,073 A * | 4/1995 | Porter ................ 227/175.1 |
| 5,409,493 A | 4/1995 | Greenberg |
| 5,417,692 A | 5/1995 | Goble et al. |
| 5,423,820 A | 6/1995 | Miller et al. |
| 5,431,660 A | 7/1995 | Burke |
| 5,462,547 A | 10/1995 | Weigum |
| 5,507,801 A | 4/1996 | Gisin |
| 5,520,691 A | 5/1996 | Branch |
| 5,529,075 A | 6/1996 | Clark |
| 5,586,985 A | 12/1996 | Putnam et al. |
| 5,591,207 A | 1/1997 | Coleman |
| 5,601,553 A | 2/1997 | Trebing et al. |
| 5,607,426 A | 3/1997 | Ralph et al. |
| 5,611,801 A * | 3/1997 | Songer ................ 606/308 |
| 5,632,745 A | 5/1997 | Schwartz |
| 5,643,267 A | 7/1997 | Hitomi et al. |
| 5,702,397 A | 12/1997 | Goble et al. |
| 5,709,687 A | 1/1998 | Pennig |
| 5,718,711 A * | 2/1998 | Berenstein et al. ................ 606/191 |
| 5,725,582 A | 3/1998 | Bevan et al. |
| 5,743,912 A | 4/1998 | Lahille et al. |
| 5,809,849 A | 9/1998 | Coffey et al. |
| 5,810,821 A | 9/1998 | Vandewalle |
| 5,827,285 A | 10/1998 | Bramlet |
| 5,893,850 A | 4/1999 | Cachia |
| 5,893,859 A | 4/1999 | Marin et al. |
| 5,899,906 A | 5/1999 | Schenk |
| 5,902,011 A | 5/1999 | Hand et al. |
| 5,928,236 A | 7/1999 | Augagneur et al. |
| 5,954,722 A | 9/1999 | Bono |
| 5,964,760 A | 10/1999 | Richelsoph |
| 5,964,763 A | 10/1999 | Incavo et al. |
| 5,976,139 A | 11/1999 | Bramlet |
| 5,984,925 A | 11/1999 | Apgar |
| 5,993,477 A | 11/1999 | Vaitekunas et al. |
| 5,997,538 A | 12/1999 | Asnis et al. |
| 5,997,541 A | 12/1999 | Schenk |
| 6,027,523 A | 2/2000 | Schmieding |
| 6,033,429 A | 3/2000 | Magovern |
| 6,039,740 A | 3/2000 | Olerud |
| 6,050,998 A | 4/2000 | Fletcher |
| 6,078,839 A * | 6/2000 | Carson ................ 607/116 |
| 6,093,188 A | 7/2000 | Murray |
| 6,143,037 A | 11/2000 | Goldstein et al. |
| 6,171,310 B1 | 1/2001 | Giordano et al. |
| 6,174,006 B1 | 1/2001 | Burt |
| 6,174,312 B1 | 1/2001 | Laminger |
| 6,179,537 B1 | 1/2001 | Anders |
| 6,183,474 B1 | 2/2001 | Bramlet |
| 6,235,062 B1 | 5/2001 | Gramnas |
| 6,245,071 B1 | 6/2001 | Pierson |
| 6,251,111 B1 | 6/2001 | Barker et al. |
| 6,261,291 B1 | 7/2001 | Talaber et al. |
| 6,319,254 B1 | 11/2001 | Giet et al. |
| 6,334,284 B1 * | 1/2002 | Provitola ................ 52/698 |
| 6,348,053 B1 | 2/2002 | Cachia |
| 6,368,326 B1 * | 4/2002 | Dakin et al. ................ 606/103 |
| 6,511,481 B2 * | 1/2003 | von Hoffmann et al. ................ 606/67 |
| 6,524,313 B1 | 2/2003 | Fassier et al. |
| 6,602,293 B1 | 8/2003 | Biermann et al. |
| 6,605,090 B1 | 8/2003 | Trieu et al. |
| 6,610,067 B2 | 8/2003 | Tallarida et al. |
| 6,629,534 B1 | 10/2003 | St. Goar et al. |
| 6,632,224 B2 | 10/2003 | Cachia et al. |

(56) References Cited

U.S. PATENT DOCUMENTS

| | | | |
|---|---|---|---|
| 6,656,184 B1 | 12/2003 | White et al. | |
| 6,656,185 B2 | 12/2003 | Gleason et al. | |
| 6,685,706 B2 | 2/2004 | Padget et al. | |
| 6,695,844 B2 | 2/2004 | Bramlet | |
| 6,736,819 B2 | 5/2004 | Tipirneni | |
| 6,840,953 B2 | 1/2005 | Martinek | |
| 6,887,243 B2* | 5/2005 | Culbert | 606/65 |
| 6,887,271 B2 | 5/2005 | Justin et al. | |
| 6,890,333 B2 | 5/2005 | von Hoffmann et al. | |
| 6,902,567 B2 | 6/2005 | Del Medico | |
| 6,908,465 B2* | 6/2005 | von Hoffmann et al. | 606/67 |
| 6,984,241 B2 | 1/2006 | Lubbers et al. | |
| 7,008,428 B2 | 3/2006 | Cachia et al. | |
| 7,033,363 B2 | 4/2006 | Powell | |
| 7,070,601 B2 | 7/2006 | Culbert et al. | |
| 7,090,676 B2 | 8/2006 | Huebner et al. | |
| 7,094,239 B1 | 8/2006 | Michelson | |
| 7,094,240 B2 | 8/2006 | Molz et al. | |
| 7,135,023 B2* | 11/2006 | Watkins et al. | 606/65 |
| 7,147,639 B2 | 12/2006 | Berki et al. | |
| 7,163,542 B2 | 1/2007 | Ryan | |
| 7,172,595 B1 | 2/2007 | Goble | |
| 7,189,251 B2 | 3/2007 | Kay | |
| 7,476,254 B2 | 1/2009 | White et al. | |
| 7,591,823 B2 | 9/2009 | Tipirneni | |
| 7,641,677 B2 | 1/2010 | Weiner et al. | |
| 7,771,428 B2 | 8/2010 | Siravo et al. | |
| 2002/0198527 A1 | 12/2002 | Muckter | |
| 2003/0036761 A1 | 2/2003 | Smothers et al. | |
| 2003/0083658 A1 | 5/2003 | Hawkes et al. | |
| 2003/0187440 A1 | 10/2003 | Richelsoph et al. | |
| 2003/0216780 A1 | 11/2003 | Fitts et al. | |
| 2004/0097943 A1 | 5/2004 | Hart | |
| 2004/0127906 A1 | 7/2004 | Culbert et al. | |
| 2004/0236424 A1 | 11/2004 | Berez et al. | |
| 2004/0243129 A1 | 12/2004 | Moumene et al. | |
| 2005/0010226 A1 | 1/2005 | Grady, Jr. et al. | |
| 2005/0143735 A1 | 6/2005 | Kyle | |
| 2005/0234456 A1 | 10/2005 | Malandain | |
| 2005/0240190 A1 | 10/2005 | Gall et al. | |
| 2005/0245933 A1 | 11/2005 | Sevrain | |
| 2005/0263549 A1 | 12/2005 | Scheiner | |
| 2005/0277940 A1 | 12/2005 | Neff | |
| 2006/0129148 A1 | 6/2006 | Simmons et al. | |
| 2006/0147127 A1 | 7/2006 | Slavin | |
| 2006/0155297 A1 | 7/2006 | Ainsworth et al. | |
| 2006/0161805 A1 | 7/2006 | Tseng | |
| 2006/0167457 A1 | 7/2006 | Suddaby | |
| 2006/0190001 A1 | 8/2006 | Powell | |
| 2006/0247638 A1 | 11/2006 | Trieu et al. | |
| 2006/0264954 A1* | 11/2006 | Sweeney et al. | 606/73 |
| 2007/0055249 A1 | 3/2007 | Jensen | |
| 2007/0123878 A1 | 5/2007 | Shaver | |
| 2007/0162019 A1 | 7/2007 | Burns | |
| 2007/0162026 A1 | 7/2007 | Tipirnini et al. | |
| 2007/0190230 A1 | 8/2007 | Trieu | |
| 2007/0233100 A1 | 10/2007 | Metzinger | |
| 2007/0260248 A1* | 11/2007 | Tipirneni | 606/65 |
| 2007/0270847 A1 | 11/2007 | Shaw | |
| 2007/0270855 A1* | 11/2007 | Partin | 606/72 |
| 2007/0276382 A1 | 11/2007 | Mikhail et al. | |
| 2008/0086144 A1 | 4/2008 | Zander | |
| 2008/0147126 A1 | 6/2008 | Tipirneni | |
| 2008/0147127 A1* | 6/2008 | Tipirneni et al. | 606/301 |
| 2008/0243191 A1 | 10/2008 | Tipernini et al. | |
| 2008/0255555 A1 | 10/2008 | Justis et al. | |
| 2008/0255560 A1* | 10/2008 | Myers et al. | 606/63 |
| 2008/0255621 A1 | 10/2008 | Fricker et al. | |
| 2008/0269746 A1* | 10/2008 | Justin | 606/62 |
| 2008/0300636 A1 | 12/2008 | Carli et al. | |
| 2009/0131936 A1* | 5/2009 | Tipirneni et al. | 606/64 |
| 2009/0131990 A1* | 5/2009 | Tipirneni et al. | 606/301 |
| 2009/0131991 A1* | 5/2009 | Tipirneni et al. | 606/301 |
| 2009/0177199 A1 | 7/2009 | Tipernini | |
| 2009/0198288 A1 | 8/2009 | Hoof et al. | |
| 2009/0254089 A1 | 10/2009 | Tipernini | |
| 2009/0254129 A1 | 10/2009 | Tipernini | |
| 2009/0306718 A1* | 12/2009 | Tipirneni et al. | 606/263 |
| 2010/0023010 A1* | 1/2010 | Nelson et al. | 606/62 |
| 2010/0114097 A1 | 5/2010 | Siravo et al. | |
| 2010/0256690 A1* | 10/2010 | Appenzeller et al. | 606/305 |
| 2010/0312245 A1 | 12/2010 | Tipirneni et al. | |
| 2010/0312292 A1* | 12/2010 | Tipirneni et al. | 606/86 R |
| 2011/0034925 A1 | 2/2011 | Tipirneni et al. | |
| 2011/0295319 A1* | 12/2011 | Duplessis et al. | 606/264 |
| 2012/0125333 A1* | 5/2012 | Bedford et al. | 128/203.25 |

FOREIGN PATENT DOCUMENTS

| | | |
|---|---|---|
| GB | 2323533 | 9/1998 |
| WO | 0067652 | 11/2000 |
| WO | 2007125561 | 11/2008 |
| WO | 2009150175 | 12/2009 |

OTHER PUBLICATIONS

Final Office Action dated Feb. 1, 2012 in U.S. Appl. No. 12/265,890.
International Search Report and Written Opinion dated Jul. 7, 2011 in Application No. PCT/US2011/033370.
Notice of Allowance dated Sep. 29, 2011 in U.S. Appl. No. 12/400,165.
Final Office Action dated Oct. 28, 2011 in U.S. Appl. No. 12/369,589.
Office Action dated Nov. 1, 2011 in U.S. Appl. No. 12/425,225.
Office Action dated Nov. 10, 2011 in U.S. Appl. No. 12/491,132.
Office Action dated Nov. 10, 2011 in U.S. Appl. No. 12/258,013.
Office Action dated Sep. 2, 2011 in U.S. Appl. No. 12/104,658.
Office Action dated Jun. 28, 2010 in U.S. Appl. No. 12/700,184.
Notice of Allowance dated Dec. 14, 2010 in U.S. Appl. No. 12/400,184.
Office Action dated Aug. 20, 2009 in U.S. Appl. No. 11/678,473.
Final Office Action mailed Feb. 19, 2010 in U.S. Appl. No. 11/678,473.
Advisory Acton mailed Apr. 14, 2010 in U.S. Appl. No. 11/678,473.
Office Action dated Aug. 6, 2009 in U.S. Appl. No. 11/742,457.
Final Office Action issued Jan. 22, 2010 in U.S. Appl. No. 11/742,457.
Advisory Action mailed Mar. 30, 2010 in U.S. Appl. No. 11/742,457.
Office Action dated Jun. 10, 2009 in U.S. Appl. No. 11/952,413.
Non-Final Office Action issued Dec. 30, 2009 in U.S. Appl. No. 11/952,413.
Final Office Action dated Jun. 29, 2010 in U.S. Appl. No. 11/952,413.
Advisory Action dated Sep. 1, 2010 in U.S. Appl. No. 11/952,413.
Office Action dated Jun. 19, 2009 in U.S. Appl. No. 11/952,715.
Advisory Action mailed on Apr. 12, 2010 in U.S. Appl. No. 11/952,715.
Office Action dated Mar. 8, 2011 in U.S. Appl. No. 12/104,328.
Office Action dated Mar. 17, 2011 in U.S. Appl. No. 12/104,658.
Advisory Action mailed Jan. 22, 2008 in U.S. Appl. No. 10/779,892.
Advisory Action mailed Feb. 2, 2007 in U.S. Appl. No. 10/779,892.
Final Office Action mailed Jan. 3, 2007 in U.S. Appl. No. 10/779,892.
Requirement for Restriction mailed Jul. 18, 2006 in U.S. Appl. No. 10/779,892.
Requirement for Restriction mailed Dec. 10, 2008 in U.S. Appl. No. 10/779,892.
Non-Final Office Action mailed Mar. 1, 2007 in U.S. Appl. No. 10/779,892.
Non-Final Office Action mailed Mar. 4, 2008 in U.S. Appl. No. 10/779,892.
Non-Final Office Action mailed Nov. 16, 2005 in U.S. Appl. No. 10/779,892.
Final Office Action mailed May 14, 2009 in U.S. Appl. No. 10/779,892.
Notice of Allowance mailed Aug. 7, 2009 in U.S. Appl. No. 10/779,892.
Final Office Action mailed Oct. 31, 2007 in U.S. Appl. No. 10/779,892.
PCT/US2008/084623 International Search and Written Opinion Report mailed Jan. 22, 2009.

(56) References Cited

OTHER PUBLICATIONS

International Preliminary Report on Patentability dated Jul. 15, 2010 in Application No. PCT/US2008/084623.
PCT/US09/057879 International Search Report and Written Opinion issued Nov. 16, 2009.
International Preliminary Report on Patentability dated Jan. 31, 2011 in Application No. PCT/US2009/057879.
PCT/US2009/061782 International Search Report and Written Opinion issued Dec. 15, 2009.
International Preliminary Report on Patentability dated Jan. 31, 2011 in Application No. PCT/US2009/061782.
PCT/US2010/023537 International Search and Written Opinion Report mailed Apr. 15, 2010.
Notice to File Missing Parts on May 12, 2010 in U.S. Appl. No. 12/769,529.
URL: http://www.cayennemedical.com/products/ifix/, Title: iFix, Source: Cayenne Medical.
Office Action dated Apr. 27, 2011 in U.S. Appl. No. 12/400,165.
Office Action dated May 11, 2011 in U.S. Appl. No. 12/369,589.
International Preliminary Report on Patentability dated Jul. 20, 2011 in Application No. PCT/US2010/023537.
Office Action dated Jun. 22, 2011 in U.S. Appl. No. 12/235,405.
Office Action Restriction dated Jun. 22, 2011 in U.S. Appl. No. 12/163,122.
Final Office Action dated Aug. 16, 2011 in U.S. Appl. No. 12/104,328.
Office Action dated Aug. 17, 2011 in U.S. Appl. No. 12/163,122.
Office Action dated Aug. 19, 2011 in U.S. Appl. No. 12/265,890.
International Search Report and Written Opinion dated Feb. 23, 2012 in Application No. PCT/US2011/048192.
Office Action dated Apr. 6, 2012 in U.S. Appl. No. 12/769,529.
Restriction Requirement dated Apr. 9, 2012 in U.S. Appl. No. 12/860,122.
Restriction Requirement dated Apr. 9, 2012 in U.S. Appl. No. 12/898,975.
Restriction Requirement dated Apr. 25, 2012 in U.S. Appl. No. 12/860,178.
Final Office Action dated Jun. 5, 2012 in U.S. Appl. No. 12/425,225.
International Preliminary Report on Patentability dated Mar. 7, 2013 in Application No. PCT/US2011/048192.
Restriction Requirement dated Mar. 28, 2013 in U.S. Appl. No. 13/118,871.
Supplementary Search Report dated Apr. 9, 2013 in European Application No. 08858204.4.
Office Action dated Apr. 9, 2013 in U.S. Appl. No. 11/952,413.
Notice of Allowance dated Nov. 6, 2013 in U.S. Appl. No. 11/678,473.
Notice of Allowance dated Nov. 6, 2013 in U.S. Appl. No. 11/742,457.
Restriction Requirement dated Nov. 13, 2013 in U.S. Appl. No. 11/952,715.
Office Action dated Nov. 22, 2013 in U.S. Appl. No. 11/952,715.
Final Office Action dated Apr. 4, 2014 in U.S. Appl. No. 11/952,715.
Notice of Allowance dated May 2, 2014 in U.S. Appl. No. 11/952,715.
Biomet, OptiLock? Periarticular Plating System for Distal Femoral Fractures, Pre-Launch 1-10 Surgical Technique, Aug. 2007, retrieved on Feb. 10, 2012, Retrieved from the Internet<URL: http://www.biomet.co.uk/resource/2051/Distal%20Femoral%20Surgical%20Tech_FINAL_8.01.07.pdf, pp. 1-28.
Notice of Allowance dated Jan. 12, 2015 in U.S. Appl. No. 14/449,555.

* cited by examiner

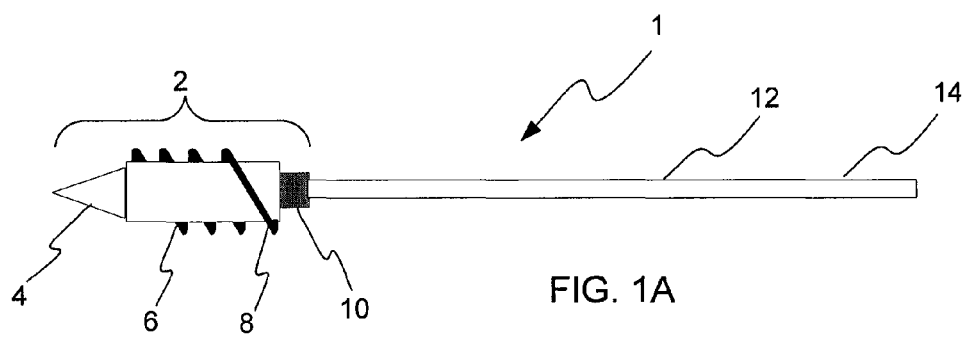
FIG. 1A
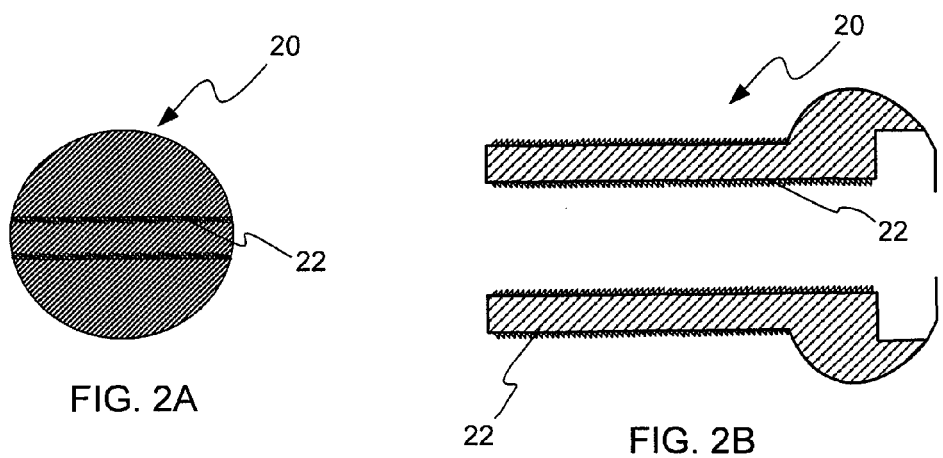
FIG. 2A
FIG. 2B
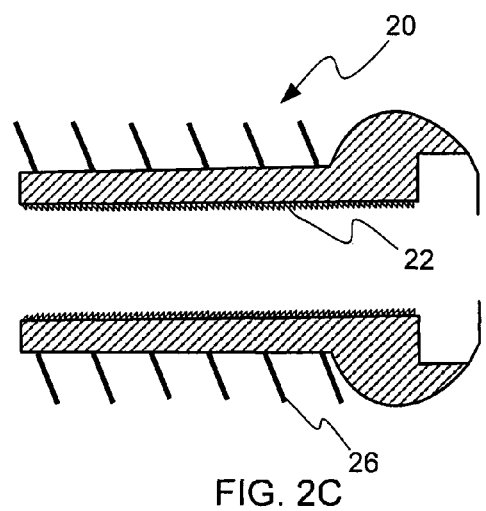
FIG. 2C

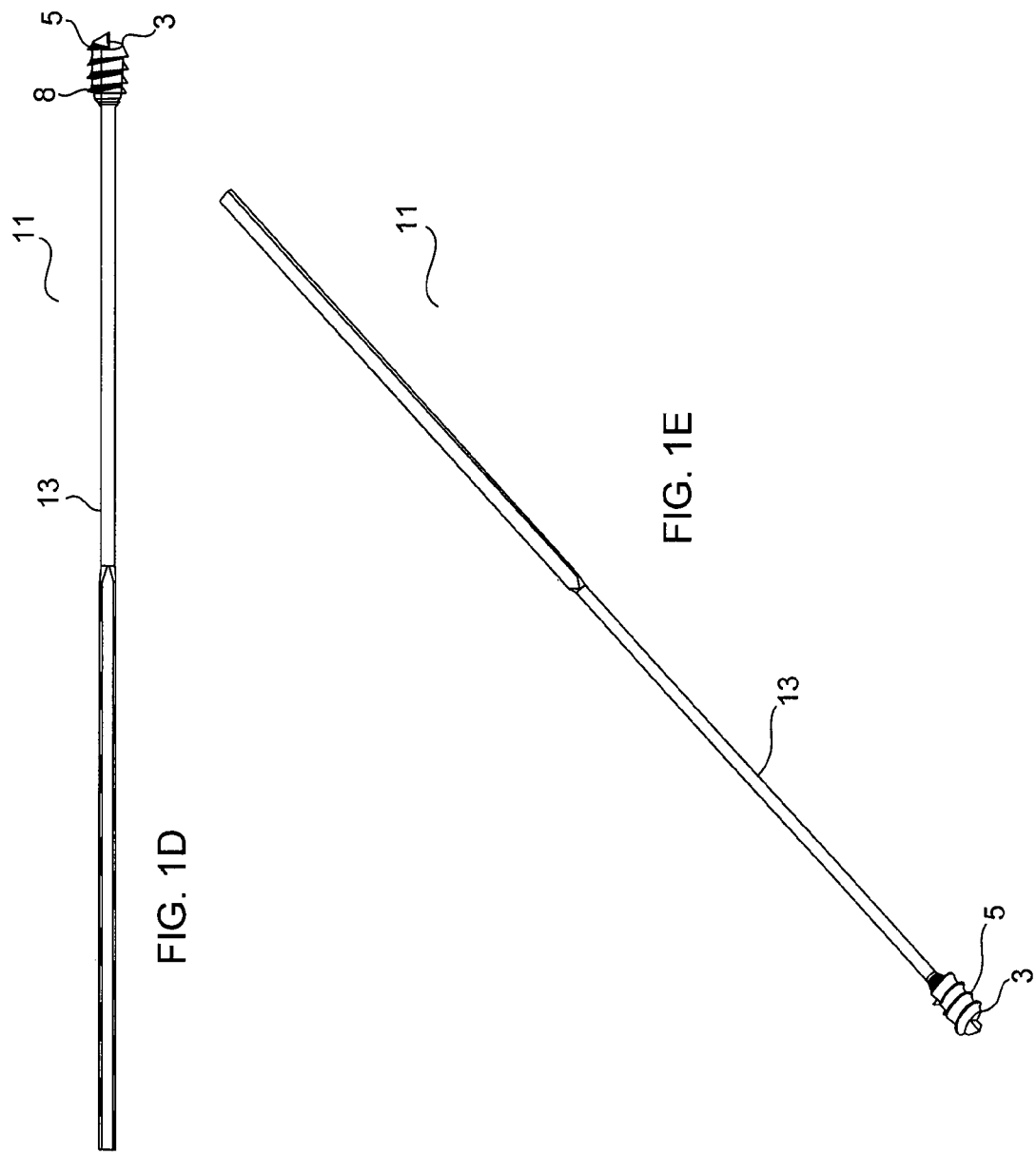

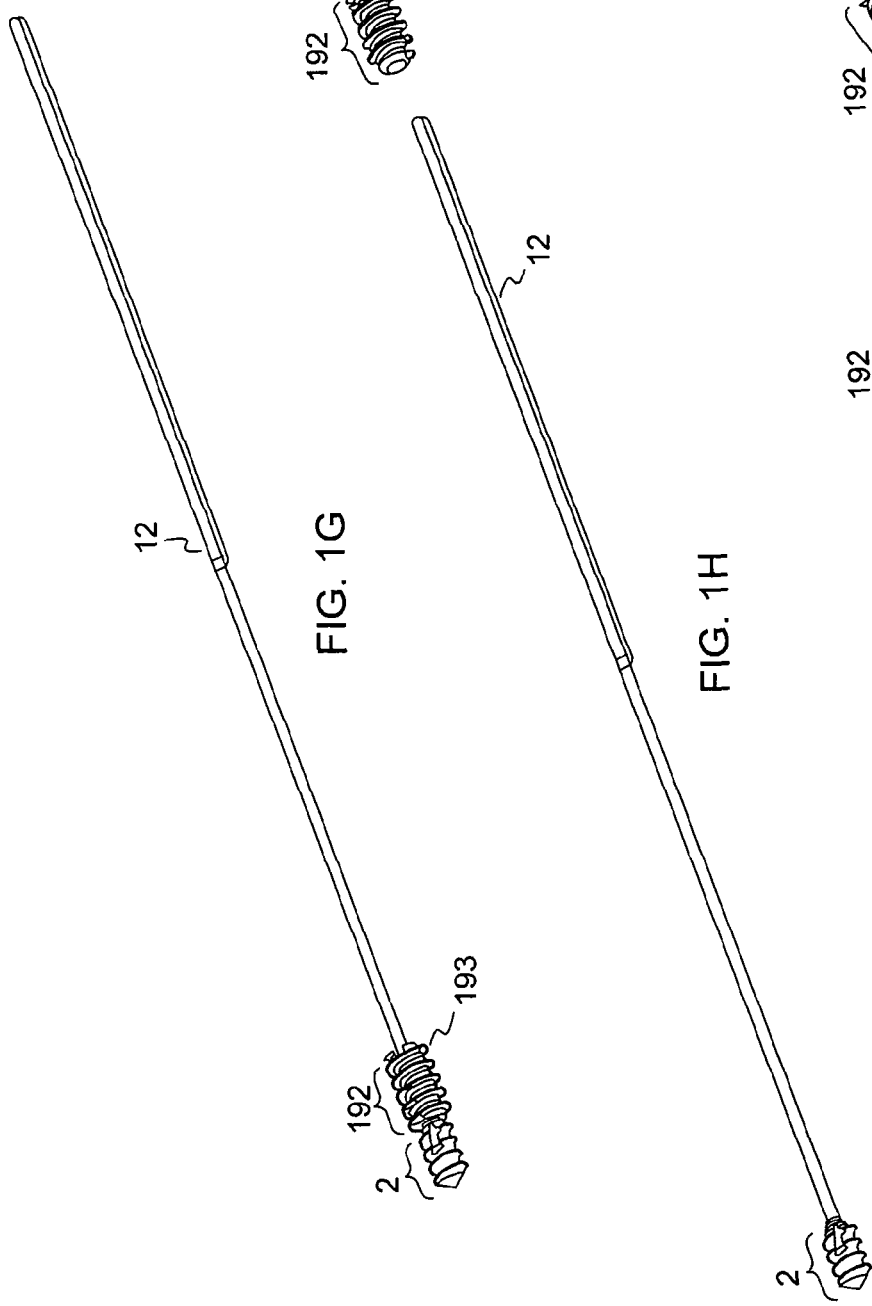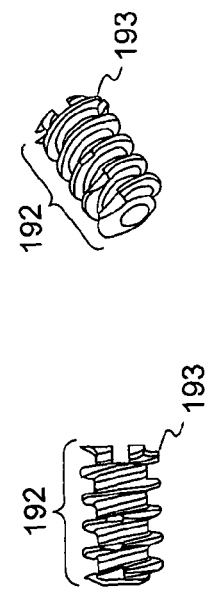

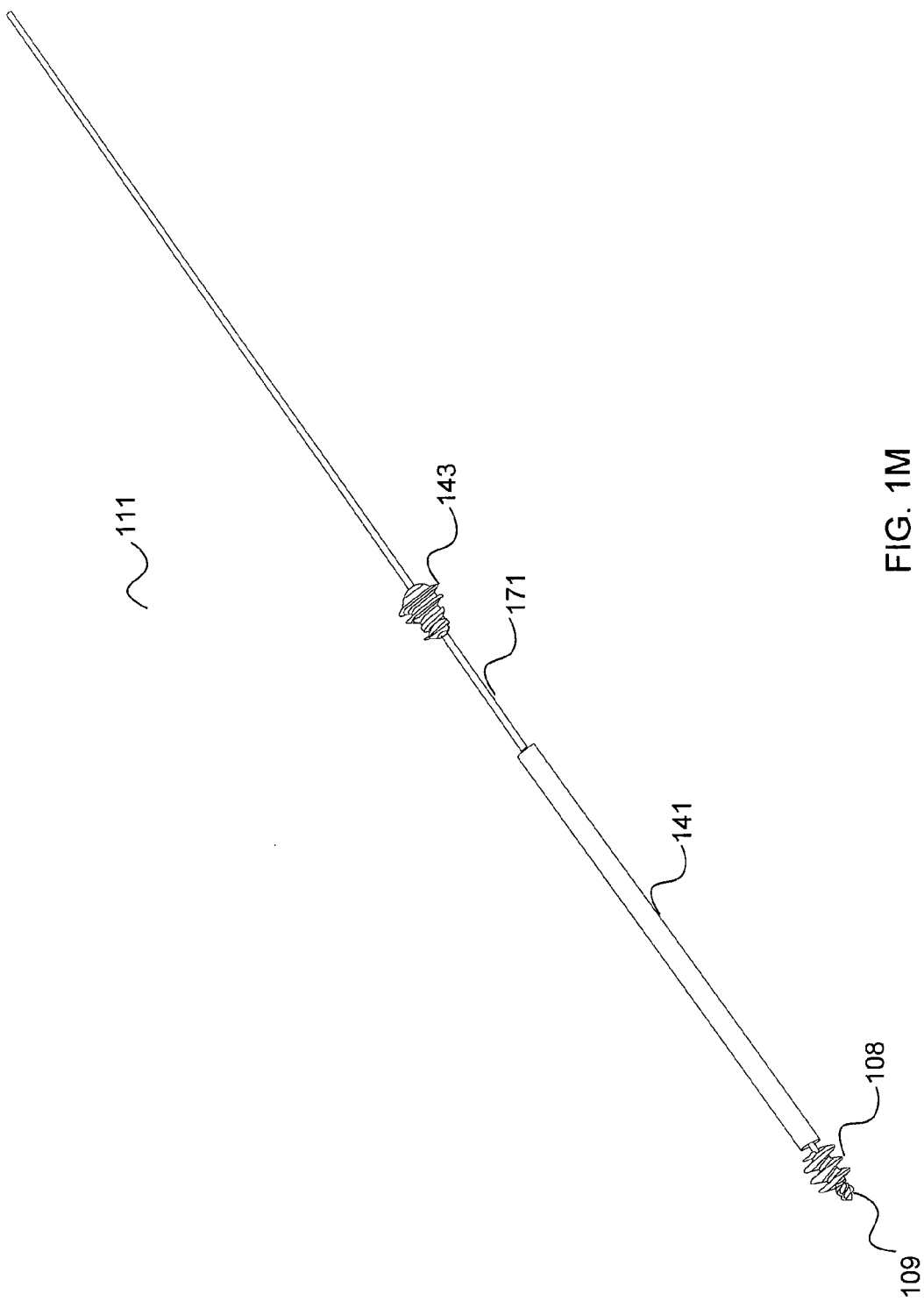

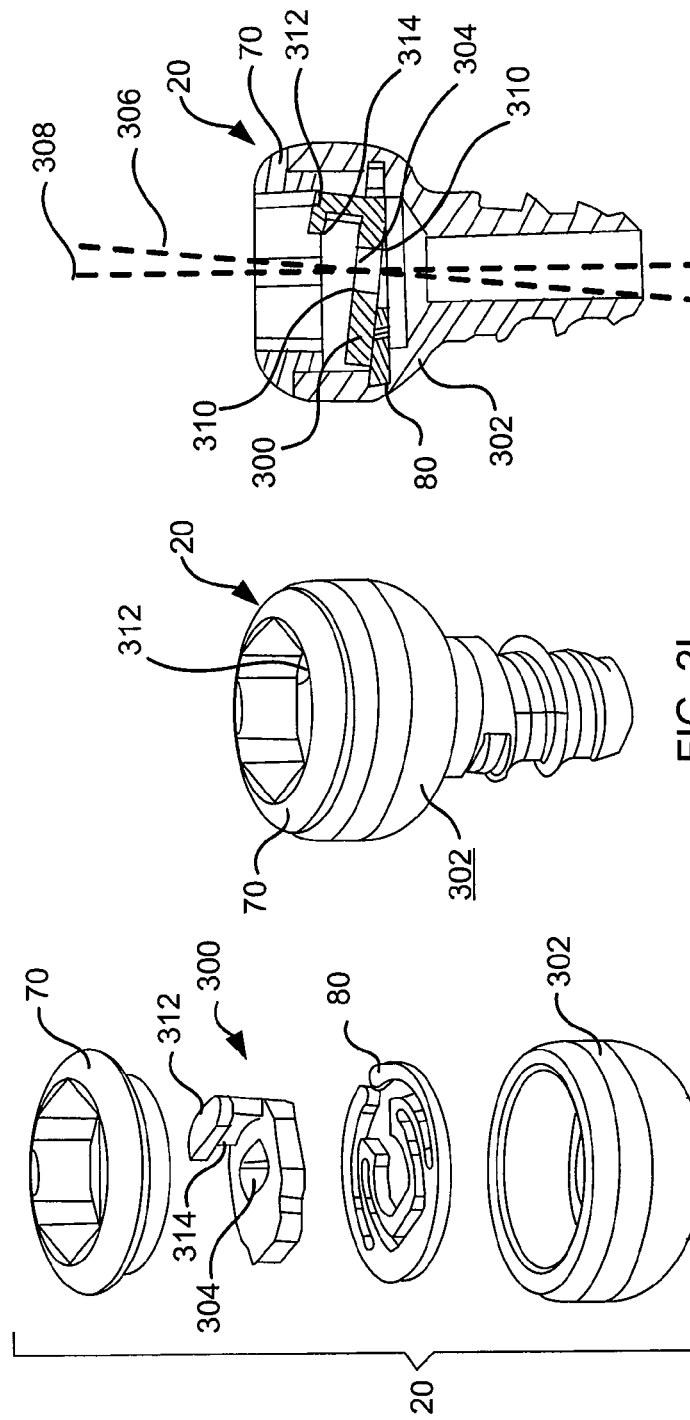

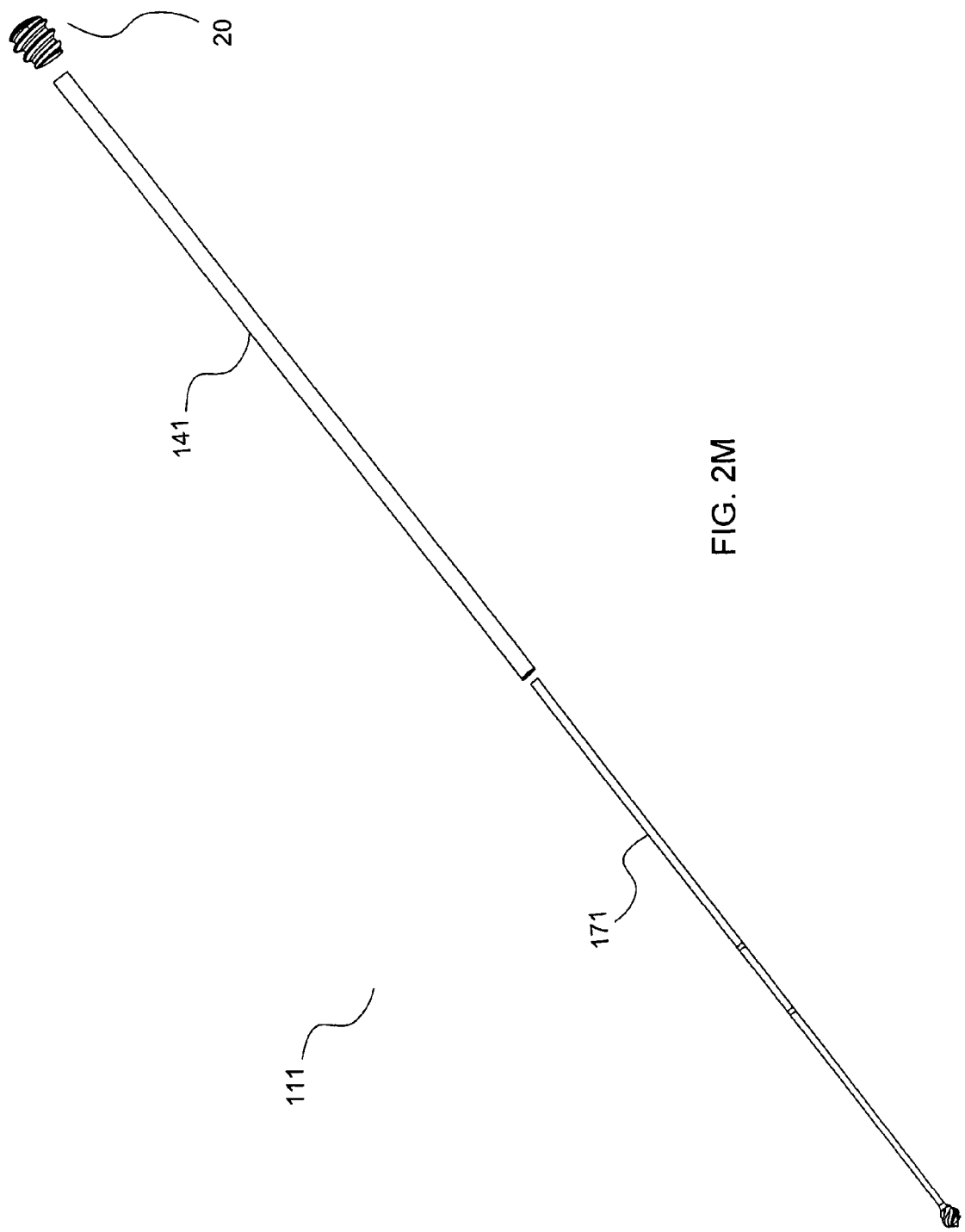

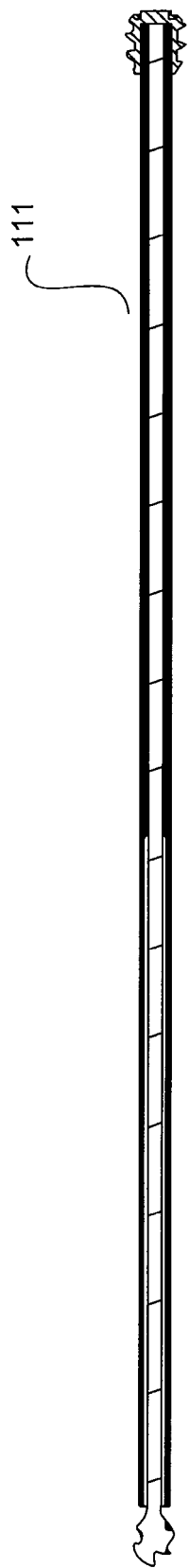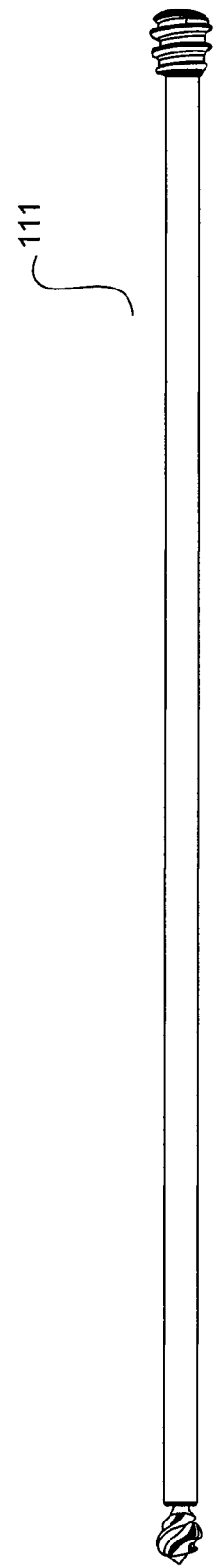
FIG. 2N
FIG. 2O

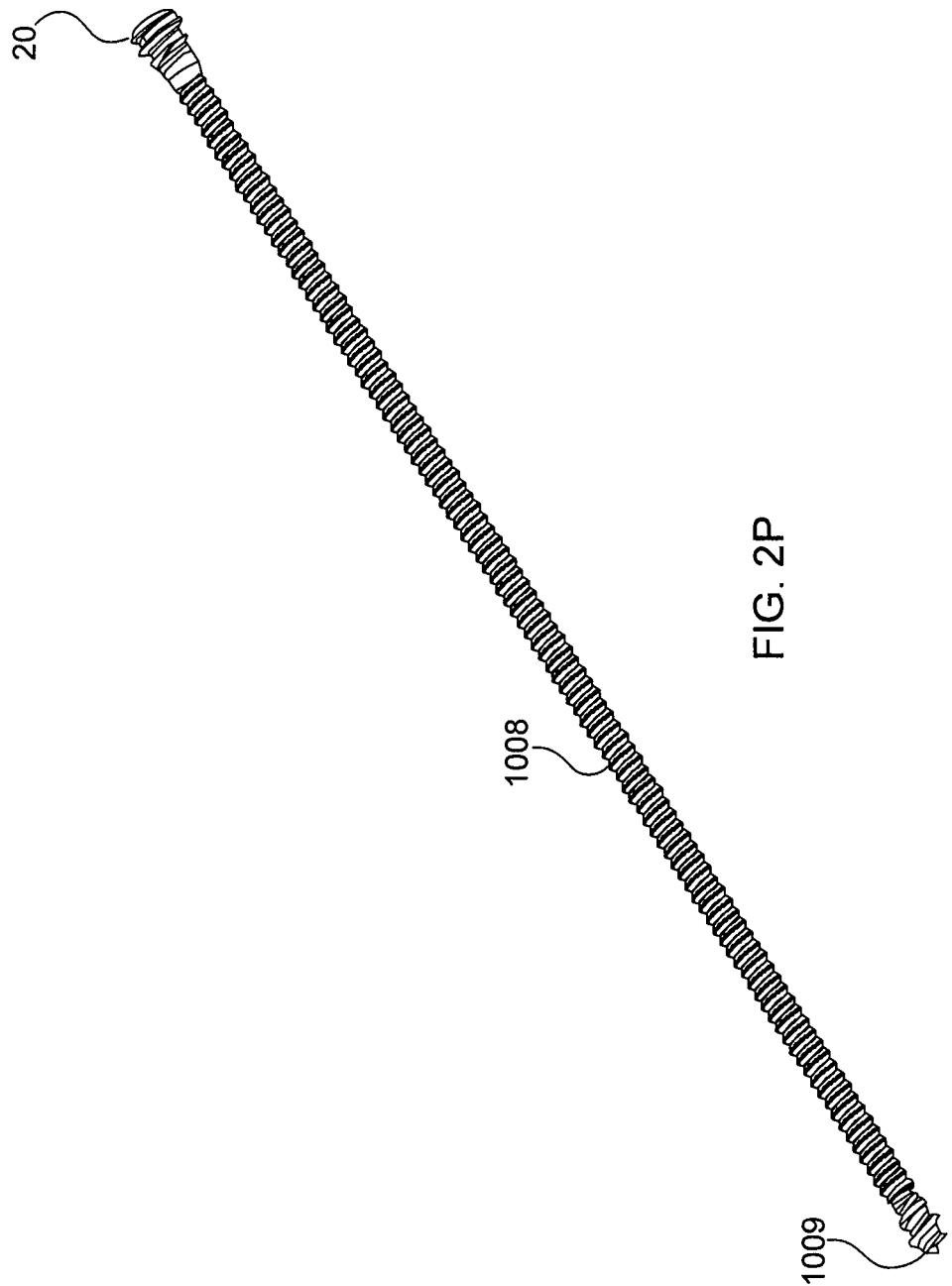

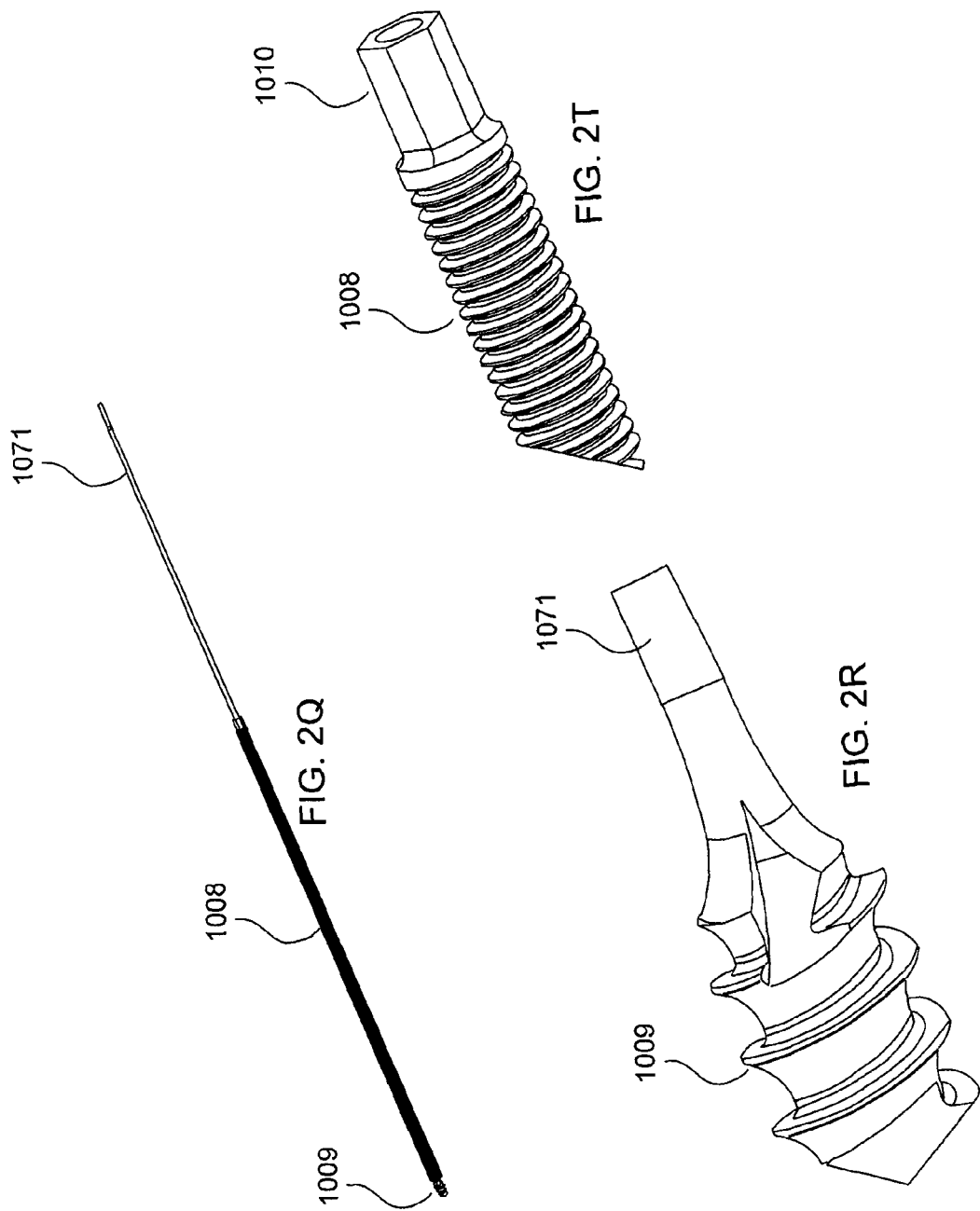

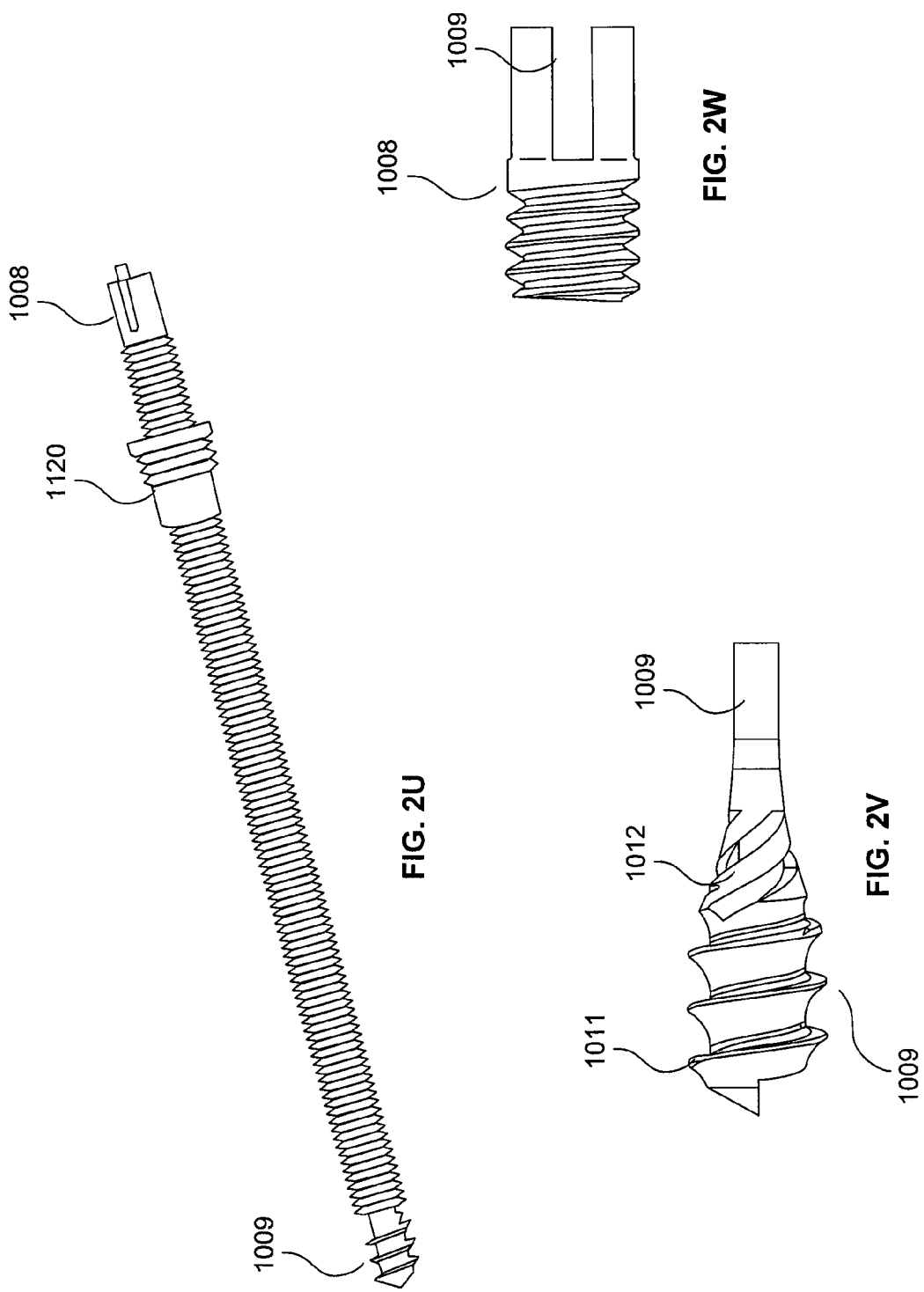

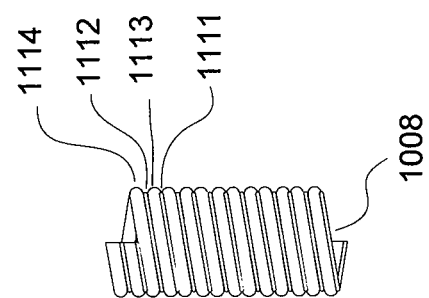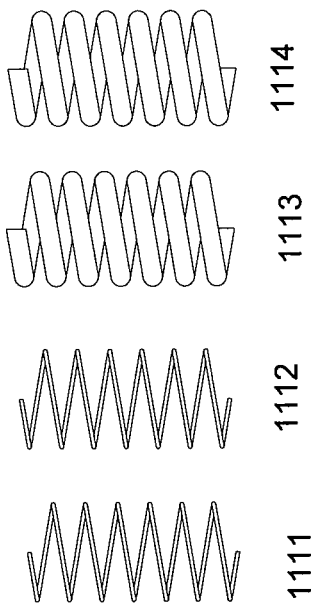

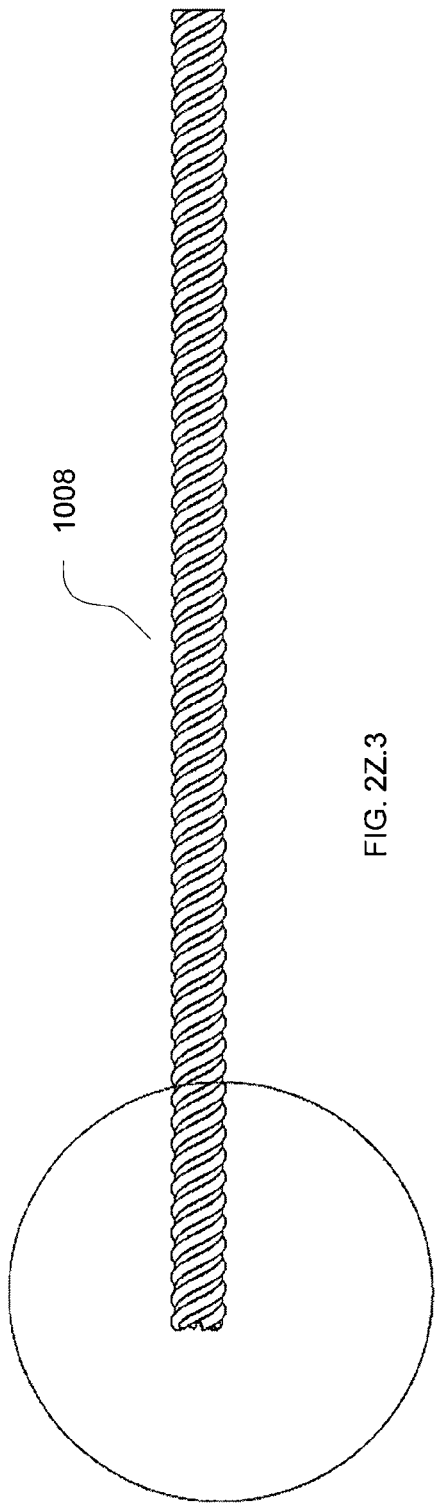
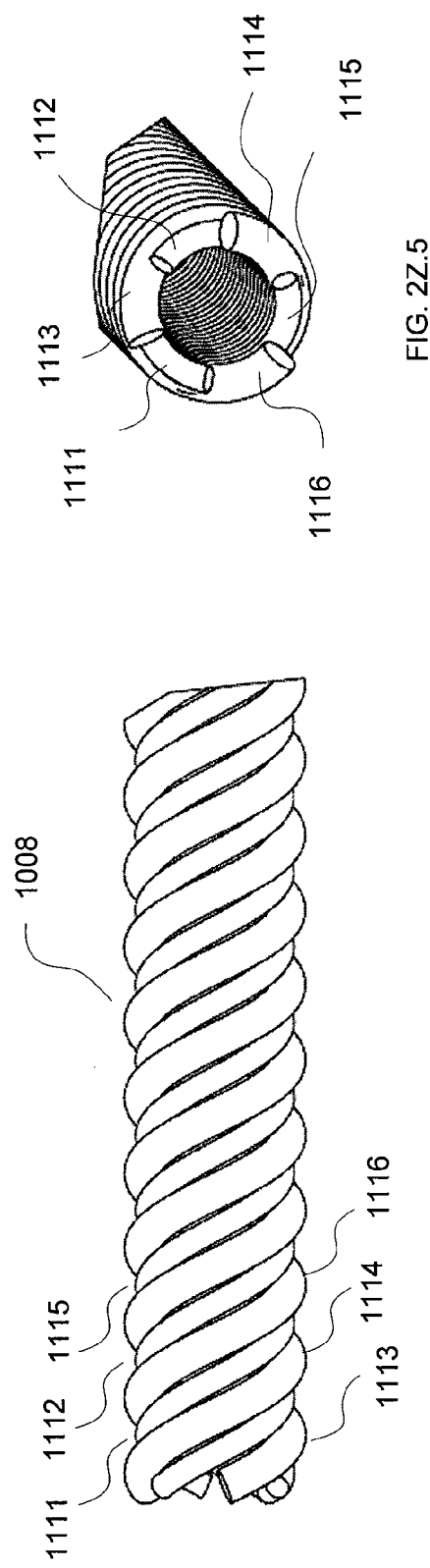
FIG. 2Z.3
FIG. 2Z.4
FIG. 2Z.5

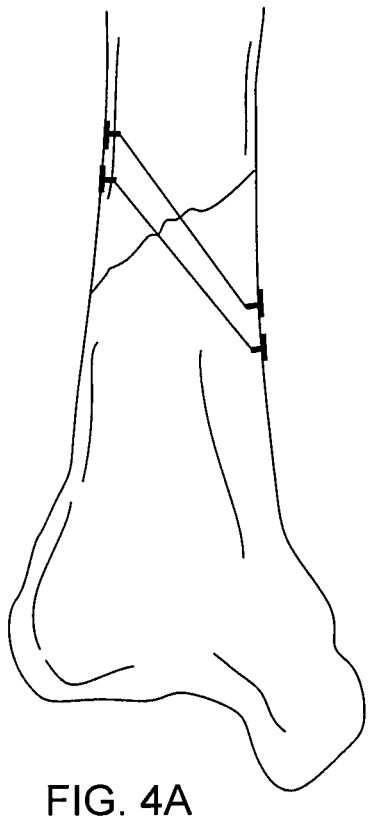
FIG. 4A     FIG. 4B
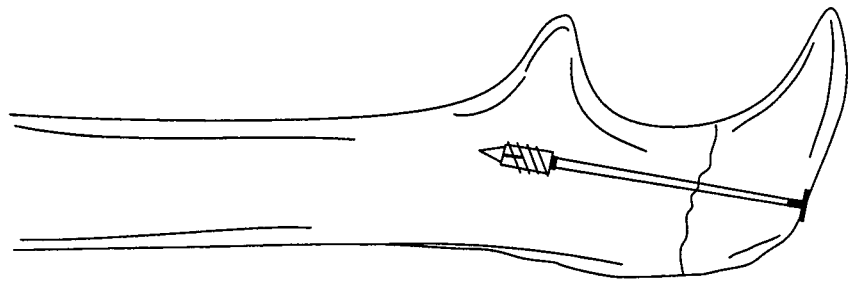
FIG. 4C

LAGWIRE SYSTEM AND METHOD FOR THE FIXATION OF BONE FRACTURES

CROSS-REFERENCE TO RELATED APPLICATIONS

This application is a continuation-in-part of, and claims priority to U.S. Ser. No. 12/898,975 filed on Oct. 6, 2010, and entitled "LAGWIRE SYSTEM AND METHOD FOR THE FIXATION OF BONE FRACTURES. The '975 application is a continuation-in-part of, and claims priority to U.S. Ser. No. 12/860,122 filed on Aug. 20, 2010, and entitled "LAGWIRE SYSTEM AND METHOD FOR THE FIXATION OF BONE FRACTURES." The '122 application is a continuation-in-part of, and claims priority to U.S. Ser. No. 12/491,132 filed on Jun. 24, 2009, and entitled "FILAMENT AND CAP SYSTEMS AND METHODS FOR THE FIXATION OF BONE FRACTURES." The '132 application is a continuation-in-part of, and claims priority to U.S. Ser. No. 12/265,890 filed on Nov. 6, 2008, and entitled "SYSTEM AND METHOD FOR THE FIXATION OF BONE FRACTURES." The '890 application is a continuation-in-part of, and claims priority to, U.S. Ser. No. 12/235,405 filed on Sep. 22, 2008, and entitled "SYSTEM AND METHOD FOR THE FIXATION OF BONE FRACTURES." The '405 application is a continuation-in-part of, and claims priority to, U.S. Ser. No. 11/952,715 filed on Dec. 7, 2007, and entitled "BONE SCREW SYSTEM AND METHOD." The '715 application is a continuation-in-part of, and claims priority to, U.S. Ser. No. 11/742,457 filed on Apr. 30, 2007, and entitled "BONE SCREW SYSTEM AND METHOD." The '457 application is a continuation-in-part of, and claims priority to, U.S. Ser. No. 11/678,473 filed on Feb. 23, 2007, and entitled "CANNULATED BONE SCREW SYSTEM AND METHOD." The '473 application is a continuation-in-part of, and claims priority to, U.S. Ser. No. 10/779,892 filed on Feb. 17, 2004, and entitled "SYSTEM AND METHOD FOR THE FIXATION OF BONE FRACTURES" (now U.S. Pat. No. 7,591,823, issued on Sep. 22, 2009). The '823 patent is a continuation of, and claims priority to, U.S. Ser. No. 10/272,773 filed on Oct. 17, 2002, and entitled "SYSTEM AND METHOD FOR THE FIXATION OF BONE FRACTURES" (now U.S. Pat. No. 6,736,819, issued on May 18, 2004). The '819 patent is the non provisional application of, and claims priority to, U.S. Provisional Application Ser. No. 60/330,187 filed on Oct. 18, 2001, and entitled "LAGWIRE SYSTEM AND METHOD." All of which are incorporated herein by reference in their entirety.

FIELD OF INVENTION

This disclosure generally relates to the fixation of fractures in one or more objects, and more particularly, to an improved system and method for the fixation of bone fractures that is operable for use without the need for guide wires.

BACKGROUND OF THE INVENTION

It is well-known in the medical arts that constant pressure on a bone fracture speeds healing. As such, orthopedic physicians may use a lagwire device to connect the bone portions and exert constant pressure on the bone fracture.

Once the lagwire is inserted into the bone fragments, it is frequently desirable to provide additional support to the wire to promote healing. Moreover, in some situations, it may be desirable for the lagwire system to allow at least some movement of the bone fragments relative to each other to promote healing, as well as be able to deliver treatments or to serve as treatment to the damaged area.

As such, a need exists for a lagwire system that: (1) provides the lagwire with additional strengthening support; (2) permits some movement of the first bone portion relative to the second bone portion; and/or (3) provides treatment to the bone portions to improve healing.

SUMMARY OF THE INVENTION

In general, the system facilitates the fixation of bone fractures. In an exemplary embodiment, the lagwire system includes an anchor component (e.g., reamer), a wire, and a sleeve. The sleeve is operable to enter a canal in a bone prepared by the anchor and wire. The sleeve may be attached to the anchor upon entry into the bone. The sleeve may include multiple coiled elements interwoven together. The canal may extend across a bone fracture allowing the sleeve to provide support across the bone fracture. A cap may also be incorporated to restrict forward and backward movement of the sleeve relative to the canal.

BRIEF DESCRIPTION OF THE DRAWINGS

A more complete understanding may be derived by referring to the detailed description and claims when considered in connection with the figures, wherein like reference numbers refer to similar elements throughout the figures, and:

FIG. 1A is a lagwire system including an anchor component and wire in accordance with an exemplary embodiment.

FIGS. 1D and 1E illustrate an embodiment of a lagwire system comprising a flexible wire and an anchor component having an improved tip geometry in accordance with an exemplary embodiment.

FIGS. 1G and 1H illustrate exemplary embodiments of a sleeve used in connection with a lagwire system.

FIGS. 1I and 1J illustrate exemplary embodiments of a sleeve.

FIG. 1M illustrates an exemplary embodiment of a lagwire device comprising an anchor component, a threaded sleeve, a tubular sleeve, and a cap.

FIG. 1O illustrates an exemplary embodiment of a cap.

FIG. 2A is a quick cap in accordance with an exemplary embodiment.

FIG. 2B is an alternative embodiment of a quick cap in accordance with an exemplary embodiment.

FIG. 2C is a screw cap in accordance with an exemplary embodiment.

FIG. 2H is an exploded perspective view a cap in accordance with an exemplary embodiment.

FIG. 2I is a perspective view of the embodiment of the cap of FIG. 2H, fully assembled.

FIG. 2J is a cross section view of the embodiment of the cap shown in FIG. 2I.

FIG. 2M is an exploded view of an exemplary embodiment of the lagwire device.

FIG. 2N is a cross section view of an exemplary embodiment of the lagwire device.

FIG. 2O is an exemplary embodiment of the lagwire device.

FIG. 2P is an exemplary embodiment of a lagwire device.

FIG. 2Q is an exemplary embodiment of a lagwire device without a cap.

FIG. 2R is an exemplary embodiment of a threaded lagwire tip.

FIG. 2T is an exemplary embodiment of an tool receiving end of a threaded sleeve.

FIG. 2U is an exemplary embodiment of a lagwire device having a threaded cap and sleeve.

FIG. 2V is an exemplary embodiment of the lagwire head of 2U.

FIG. 2W is an exemplary embodiment of the driver surface of the sleeve of 2U.

FIG. 2Z.1 is an exemplary embodiment of components of a sleeve shown separately.

FIG. 2Z.2 is an exemplary embodiment of interwoven components of a sleeve having four fibers.

FIG. 2Z.3 is an exemplary embodiment of interwoven components of a sleeve having six fibers.

FIG. 2Z.4 is an enlarged exemplary embodiment a sleeve having six fibers.

FIG. 2Z.5 is an exemplary embodiment of an end view of a sleeve having six fibers.

FIG. 4A is a fixation of a bone fracture in accordance with an exemplary embodiment.

FIGS. 4B-4D are fixations of fractures of a certain portions of a bone in accordance with an exemplary embodiment.

DETAILED DESCRIPTION

Figure 1B:
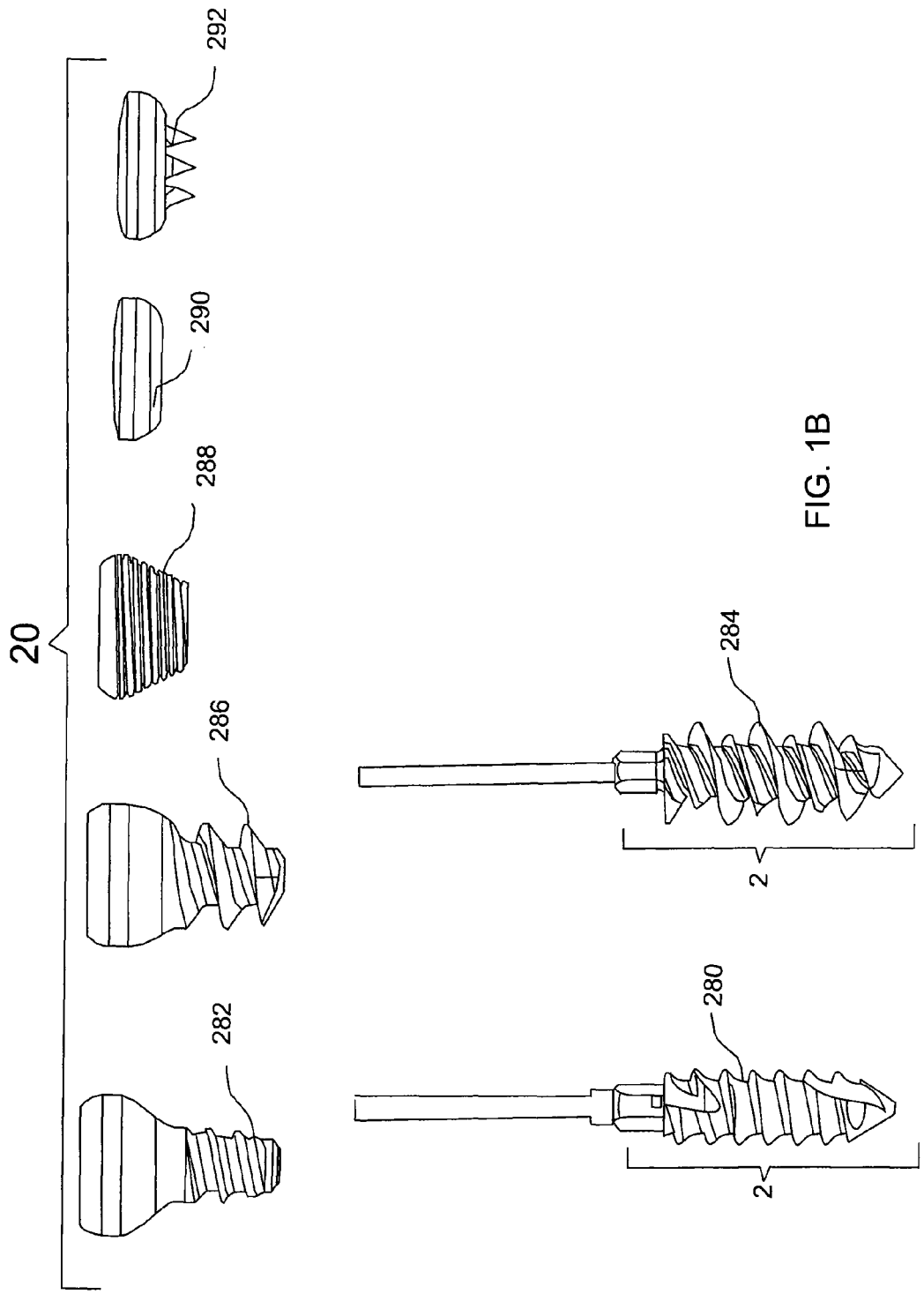
FIG. 1B is a lagwire system illustrating various thread combinations as embodiments.

The present disclosure includes various exemplary embodiments in sufficient detail to enable those skilled in the art to practice the inventions, and it should be understood that other embodiments may be realized without departing from the spirit and scope of the inventions. Thus, the following detailed description is presented for purposes of illustration only, and not of limitation, and the scope of the inventions is defined solely by the appended claims. The particular implementations shown and described herein are illustrative of the invention and its best mode and are not intended to otherwise limit the scope in any way.

In general, the present system facilitates the change in distance between objects, object portions, or surfaces, compresses objects or object portions together, and/or provides a configurable or random amount of pressure between surfaces. The system may facilitate changing, maintaining, reducing and/or expanding the distance between objects or object portions. The applied pressure may be suitably configured to be constant, increasing, decreasing, variable, random, and/or the like. In an exemplary embodiment, the system includes a device which may be fixedly or removably attached to pathology, such as to a certain portion of a bone. In a particular embodiment, the device is fixedly or removably attached to the far cortex of the bone. In another embodiment, the disclosure includes a device or method for retracting the attached device to reduce the distance between the surfaces of the pathology. In a further embodiment, the disclosure includes a device and/or method for maintaining the pressure between the surfaces of pathology. In various embodiments, the system is configured to provide improved healing of a fracture and/or the surrounding tissue.

In an exemplary embodiment, and as shown in FIGS. 1 and 2, the lagwire system 1 includes a head or anchor component 2 (e.g., reamer), a wire 12 and a cap 20. The lagwire system 1 may be fabricated using any type, amount or combination of materials suitably configured for the particular application. In an exemplary embodiment for medical applications, the lagwire system 1 is fabricated with stainless steel, titanium and/or titanium alloy which minimize reactivity with the body. Each component may be fabricated with various diameters, thread pitches, lengths and/or the like. The anchor component 2 may include threads, fins, tines, or any other fixation device or structure capable of securing the anchor component 2 to an object. Wire 12 may form any cross-sectional shape, width, thickness, diameter, and surface features along its length, and thus, for example, may form a simple cylinder and/or may include ribs, threads, serrations, one or more flat surfaces, bumps, and/or roughened surfaces along its length. These and other various characteristics of lagwire system 1 enable it to self guide through various soft tissues and bone.

Certain exemplary components of the system will now be discussed. The anchor component 2 is any device which is configured to fixedly or removably attach to any object, such as pathology. In a particular embodiment, the anchor component 2 is configured to be fixedly or removably attached to the far cortex of the bone, as shown in FIGS. 4A-4G. As best shown in FIG. 1A, the anchor component 2 may include, for example, a self drilling tip 4 device which is suitably configured to puncture a hole and/or guide the anchor component 2, self cutting threads 6 which are suitably configured to cut thread grooves into the inside surface of a hole, fastening threads 8 which are suitably configured to mate with the newly formed thread grooves, and a tool attachment 10 suitably configured for mating with a tool head (e.g., hex head wrench, socket wrench, Phillips screwdriver, flathead screwdriver, alien wrench and/or the like).

Anchor component 2 may include different and interchangeable thread configurations, lengths, diameters, pitches and the like to facilitate insertion into different types of bone or other structures (e.g., cortical bone, cancellous bone, etc). Similarly, cap 20 my include different thread configurations, lengths, diameters, pitches and the like to facilitate insertion into different types of bone or other structures. For example, both the anchor component 2 and/or cap 20, may be interchangeably removed and replaced by different anchor components 2 and caps 20 with different thread configurations. Alternatively, the anchor component 2 may not be removable from the remainder of the wire 12.

Examples of such thread configurations are illustrated in FIG. 1B and may be adapted for insertion into various bone or other structures. In one embodiment, the anchor component 2 includes leading threads 280 accommodating insertion into cortical bone while the cap 20 includes trailing threads 282 accommodating insertion into cortical bone. In another embodiment, the anchor component 2 includes leading threads 284 accommodating insertion into cancellous bone while the cap 20 includes trailing threads 286 accommodating insertion into cancellous bone. In another embodiment, the anchor component 2 includes leading threads 280 accommodating insertion into cortical bone while the cap 20 includes trailing threads 286 accommodating insertion into cancellous bone. In another embodiment, the anchor component 2 includes leading threads 284 accommodating insertion into cancellous bone while the cap 20 includes trailing threads 282 accommodating insertion into cortical bone. In another embodiment, the anchor component 2 includes leading threads 280 accommodating insertion into cortical bone while the cap 20 includes trailing threads 288 accommodating insertion a mechanical component such as a plate anchored into bone. In another embodiment, the anchor component 2 includes leading threads 284 accommodating insertion into cancellous bone while the cap 20 includes trailing threads 288 accommodating insertion a mechanical component such as a plate anchored into bone. In another embodiment, the anchor component 2 includes leading threads 280 accommodating insertion into cortical bone while the cap 20 includes a low-profile button-like design 290 that butts against the bone or a mechanical component. In another embodiment, the anchor component 2 includes leading threads 284 accommodating insertion into cancellous bone while the cap 20 includes a low-profile button-like design 290 that butts against the bone or a mechanical component. In another embodiment, the anchor component 2 includes leading threads 280 accommodating insertion into cortical bone while the cap 20 includes a low-profile button-like design that butts against the bone or a mechanical component and may also include spikes or teeth 292 to prevent rotation of the cap 20. In another embodiment, the anchor component 2 includes leading threads 284 accommodating insertion into cancellous bone while the cap 20 includes a low-profile button-like design that butts against the bone or a mechanical component and may also include spikes or teeth 292 to prevent rotation of the cap 20.

In an exemplary embodiment, the anchor component may comprise any geometry that suitably allows the anchor component to partially or fully move forward if exposed to material, such that it will glance off (e.g., deflect off of or move away from) the surrounding bone when traveling through a bone canal. Moreover, the anchor component may be flexible or inflexible.

Figure 1C:
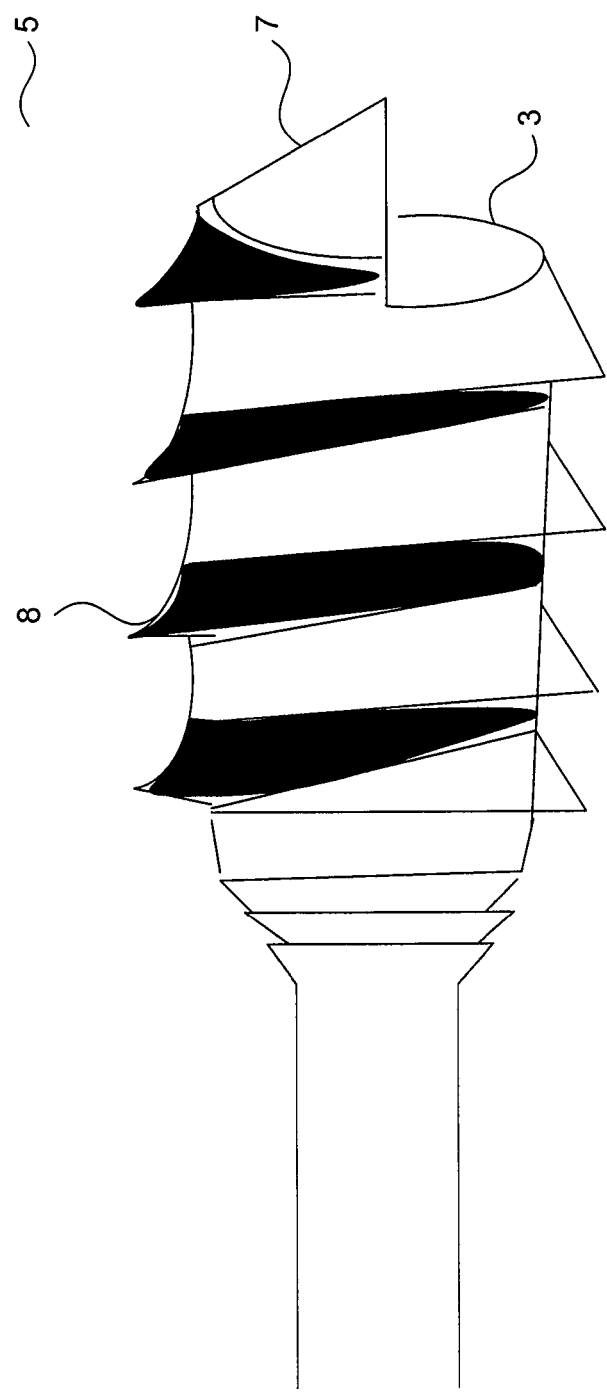
FIG. 1C illustrates an embodiment of an anchor component having an improved tip geometry in accordance with an exemplary embodiment.

For example, FIG. 1C illustrates an embodiment of anchor component 5 comprising tip 3 and cutting threads 8. As shown, tip 3 comprises a partially or fully substantially planar surface and pointed cutting edge 7. However, it will be understood by one skilled in the art that the tip and cutting edge may comprise any desired gradient. For example, the tip and cutting edge may be adjusted to be flatter or sharper depending upon various factors, such as the strength of the bone and desired rate of advancement through the canal. For example, if a patient's bones are brittle, a flatter point angle may be used to avoid or minimize puncturing of the bone.

Moreover, in one embodiment, the anchor component permits forward movement of the device, but prevents or minimizes rearward translation. For example, the shape of helical threads 8 may permit forward movement, while restricting or minimizing rear movement.

In another embodiment of a system 1, the cap 20 may be placed at both ends of the wire 12, and any combination of caps 20 threads or additional features may be used as preferred by an operator of the system 1. For example, in one embodiment, a first cap 20 includes cortical threads 282, cancellous threads 286, machine threads 288 accommodating insertion a mechanical component such as a plate anchored into bone, a low-profile button-like design 290 that butts against the bone or a mechanical component, and/or spikes or teeth 292 to prevent rotation of the first cap 20; and a second cap 20 includes cortical threads 282, cancellous threads 286, machine threads 288 accommodating insertion a mechanical component such as a plate anchored into bone, a low-profile button-like design 290 that butts against the bone or a mechanical component, and/or spikes or teeth 292 to prevent rotation of the second cap 20.

In a particular embodiment, the tip is on the front end of anchor component 2, followed by the cutting threads 6, the fastening threads 8, the tool attachment 10, then wire 12. The elements of anchor component 2 may be fabricated as one component or one or more elements may be configured to be removably or fixedly mated together to form anchor component 2. If mated together, a particular element may be exchanged for different applications. For example, if anchor component 2 needs to be inserted into a dense or hard bone, a stronger or sharper tip 4 may be screwed into thread element 6,8. Moreover, if deeper thread grooves are desired, cutting threads 6 may be replaced with greater diameter threads. Furthermore, if a different tool head is incorporated into a drill, tool attachment 10 may be exchanged with the appropriate attachment.

In one embodiment, the outside diameter of the fastening threads are similar to the thread diameters of known surgical screw sizes. Exemplary outside diameters of cortical anchor components include 3.5 mm and 4.5 mm, wherein the length of the thread section is similar to the cortex thickness. Exemplary outside diameters of cancellous (i.e., little or no cortex) anchor components include about 4.0 mm and 6.5 mm, wherein the length of the thread section may be about 16 mm or 32 mm.

Wire 12 is any device suitably configured, when force is applied, to reduce the distance between two surfaces. In one embodiment, wire 12 is configured to retract the anchor component 2 device to reduce the distance between the surfaces of the pathology. In one embodiment, anchor component 2 and wire 12 are constructed as one component. In another embodiment, anchor component 2 and wire 12 are constructed as separate components, but the components are configured such that the anchor component 2 may be threaded onto wire 12 after wire 12 is placed into the bone. Wire 12 further includes an interface component 14 on at least a portion of its surface, wherein the interface component 14 is suitably configured to limit the movement of cap 20 to move distally toward anchor component 2, but not proximally (backwards).

In an exemplary embodiment, interface component 14 of wire 12 includes a sawtooth like configuration such that one side of each tooth (e.g. the side closest to anchor component 2) is substantially perpendicular to the surface of wire 12, while the other side of the sawtooth is at a suitable angle, such as 45 degrees, thereby forming a triangular pattern for each sawtooth. In this manner, the inverse sawtooth on the inside surface of the cap slides or bends over the angled side of the wire sawtooth, but the substantially perpendicular side of the wire sawtooth restricts or limits the cap sawtooth from backwards movement. In another embodiment, any portion or the entire length of wire 12 includes any configuration such as, for example, round, oval, flat on one or more portions of the wire, and/or microgrooves or ridges along the wire (which may include the sawtooth configuration, indentions or other configurations) to increase the friction along the wire. In one embodiment, wire 12 holds 20 pounds of pull; however, microgrooves in the wire may significantly increase the strength of the wire 12.

In an exemplary embodiment, wire 12 is comprised of a thin metal such as, for example, stainless steel, titanium and/or titanium alloy, so it may be easily cut to almost any desired length.

In one embodiment, the wire is flexible such that the wire can be bent to navigate through an object, such as a bone canal. FIGS. 1D and 1E illustrate different views of an exemplary embodiment of lagwire system 11 comprising flexible wire 13 and anchor component 5 (illustrated in FIG. 1C).

Figure 1F:
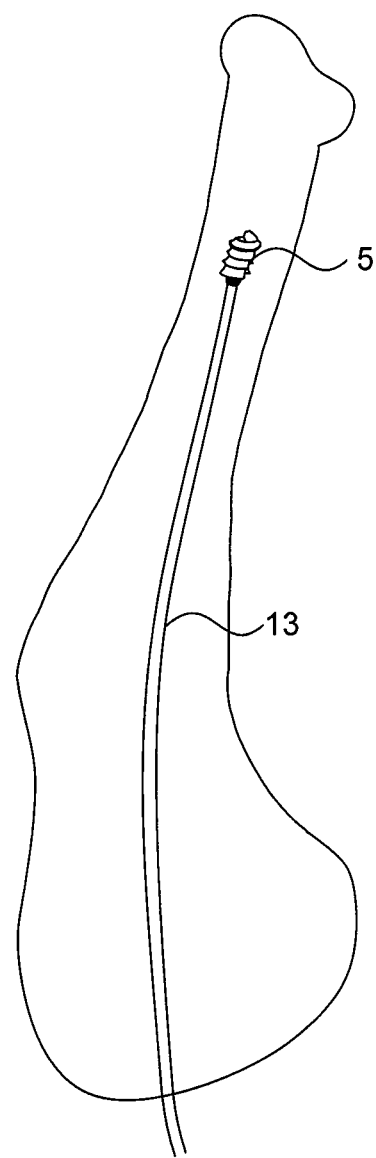
FIG. 1F illustrates an exemplary lagwire system navigating through a bone canal in accordance with an exemplary embodiment.

FIG. 1F illustrates use of an embodiment of a lagwire system within a non-linear bone canal. As shown, flexible wire 13 is operable to bend to allow the system to maneuver through both linear and non-linear bone canals. The configuration of anchor component 5 is operable to glance off the surrounding bone while traveling through the bone canal, such that the anchor will not break through and cause damage to the bone.

The lagwire system may be inserted into a bone using any manual or automatic device that suitably rotates the anchor component. Moreover, the lagwire system may be inserted with or without a guide wire or other stabilizing device.

In various embodiments, the lagwire system comprises an anchor component (e.g., reamer), one or more sleeves (such as threaded sleeve and/or tubular sleeve), and a cap. For example, FIGS. 1M-1P illustrate lagwire system 111 comprising reamer 109, wire 171, threaded sleeve 108, tubular sleeve 141 and cap 143.

The tubular sleeve may be any structure operable for insertion over the wire to provide additional stability to the wire. For example, FIG. 1M illustrates an exemplary embodiment of tubular sleeve 141 having a substantially smooth exterior surface and a shape that substantially conforms to the shape of the lagwire 171 (i.e., cylindrical). However, it will be understood that the sleeve may be any desired material, length, diameter, size and/or shape (e.g., square, triangular, elliptical). In various embodiments, the exterior surface of the tubular sleeve may comprise one or more gripping means. The sleeve may be configured with sufficient strength and shape that it may be inserted into a previously (partially or fully) reamed bone canal without the support of the wire (or with minimal support).

Figure 1L:
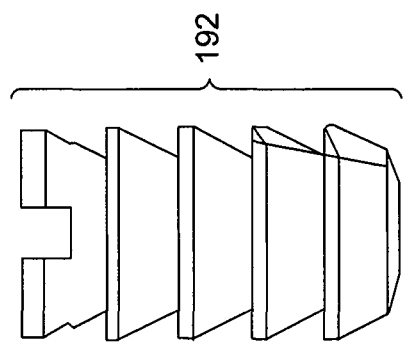
FIGS. 1K and 1L illustrate exemplary embodiments of a sleeve comprising a "Christmas Tree" configuration.
Figure 1K:
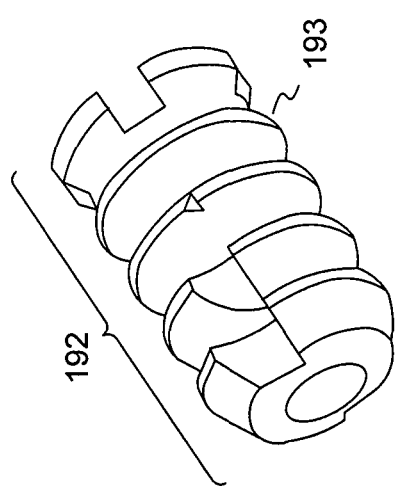
Figure 1N:
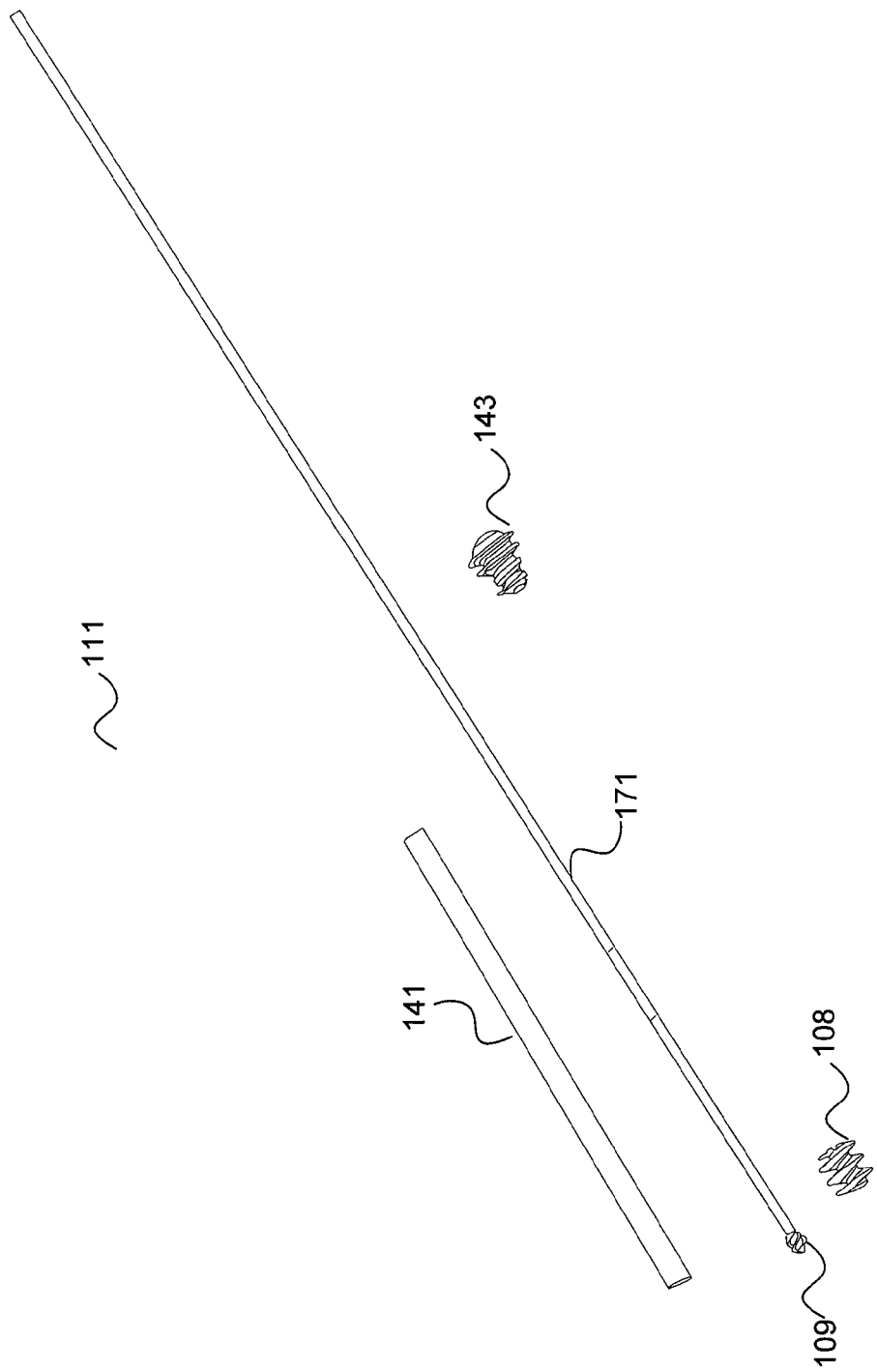
FIG. 1N illustrates an exemplary embodiment of an anchor component and threaded sleeve.
Figure 10:
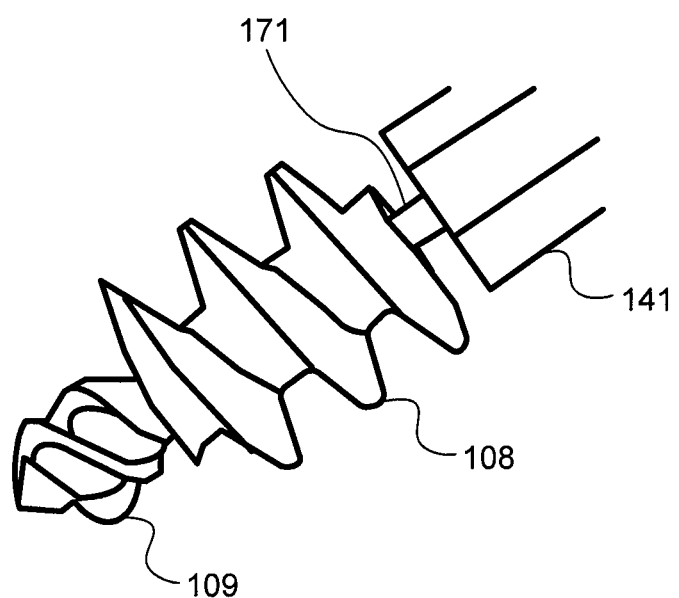
Figure 1P:
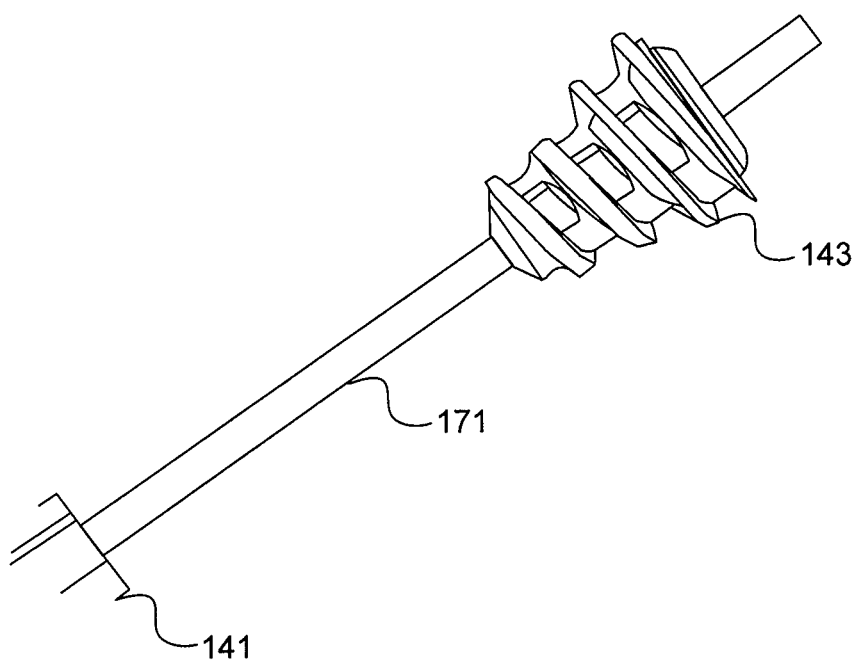
FIG. 1P illustrates an exemplary embodiment of the anchor component, threaded sleeve, tubular sleeve and cap of a lagwire system.

The threaded sleeve may be any structure having a gripping component on an exterior and/or interior surface. A gripping component may be any material, structure, device or shape that increases the holding strength of the lagwire. For example, as illustrated in FIG. 1M, threaded sleeve 108 has a gripping component comprising a threaded surface. In various embodiments, the gripping component may comprise threads, barbs, a ribbed surface or any other gripping component which enhances holding strength. Moreover, the gripping component may comprise any desired configuration. For example, FIGS. 1K and 1L illustrate sleeve 192 comprising gripping component 193 having a "Christmas Tree" configuration.

FIGS. 1G-1J illustrate exemplary embodiments of a threaded sleeve 192 comprising threaded external surface 193. As shown in FIG. 1G, threaded sleeve 192 may be positioned so as to abut anchor component 2, and/or threaded sleeve 192 may comprise a component for joining sleeve 192 to anchor component 2 (such as threads 193). In other embodiments, threaded sleeve 192 may be positioned at any desired location along the length of lagwire 12. Moreover, in some embodiments, the sleeve may comprise a locking mechanism, such as threads and/or the like, to affix the sleeve at a desired position.

FIG. 1H illustrates threaded sleeve 192 having a tubular configuration so as to be operable to slide along the length of lagwire 12. In other embodiments, threaded sleeve 192 may be integrally formed with lagwire 12.

As shown in FIG. 1M, tubular sleeve 141 abuts threaded sleeve 108, and threaded sleeve 108 abuts reamer 109. However, it will be understood that tubular sleeve 141 and threaded sleeve 108 may be positioned at any desired location along wire 171. For example, in an embodiment, tubular sleeve 141 may be positioned so as to bridge a bone fracture.

The threaded sleeve and tubular sleeve may partially or fully comprise any suitable material, such as plastic (e.g., polyetherketone (PEEK)), steel, titanium, titanium alloy, and/or the like, and may be flexible or inflexible. Moreover, these materials may be incorporated onto or into any or all of the parts, components, and/or devices discussed herein (e.g. wire, anchor, cap, sleeve, etc.)

With continued reference to FIGS. 1M-1P, it will be understood that any of reamer 109, threaded sleeve 108 and/or tubular sleeve 141 may be separate components or may be integrally formed together as one component. For example, the threaded sleeve and the tubular sleeve may be formed as one component. It will also be understood that threaded sleeve and tubular sleeve may be any desired length. For example, as illustrated in FIG. 2P, a threaded sleeve 1008 may extend the entire length of the wire between head 1009 and cap 1120. In another example, as illustrated in FIG. 2Q, threaded sleeve 1008 may extend a portion of the length of wire 1071.

In various embodiments, head 1009 may be configured to receive an end of threaded sleeve 1008 such that the threads between head 1009 and threaded sleeve 1008 are suitably contiguous. In another embodiment, threaded sleeve 1008 and cap 1120 may be configured such that their threads are suitably contiguous when abutted end to end. As illustrated in FIG. 2R, wire 1071 may mate with head 1009 in a configuration that allows threaded sleeve 1008 to abut head 1009 creating suitably contiguous threads between head 1009 and threaded sleeve 1008.

In another embodiment, one or more ends 1010 of threaded sleeve 1008 (and/or tubular sleeve 141) may have a surface configured to receive a driver. For example, as illustrated in FIG. 2T, threaded sleeve 1008 may have a hexagonal end 1010 configured to receive any of a variety of hexagonal drivers. In another example, as illustrated in FIG. 2W, threaded sleeve 1008 may have multiple arc lobes 1013 for receiving a driver. Any surface or driver capable of providing suitable torque for driving the sleeve may be incorporated.

In other embodiments, as shown in FIG. 2V, head 1009 may be configured with tapered left handed threads 1012 behind cutting threads 1011. The tapered left handed threads 1012 may cut into sleeve 1008. By threading sleeve 1008 over lagwire 1071, sleeve 1008 can advance until it contacts head 1009. In contacting head 1009, tapered left handed threads 1012 may cut into sleeve 1008, securing sleeve 1008 to lagwire 1071. The secured engagement between head 1009 and sleeve 1008 allows a user to back both the lagwire 1071 and sleeve 1008 out of a bone at the same time.

In accordance with one embodiment, threaded sleeve 1008 may be used to fixate a fractured bone and aid in healing by drilling a hole into at least two bone fragments. Sleeve 1008 is configured to provide fixation of a fracture at specified lengths. Sleeve 1008 is further configured to provide increased stabilization across the fracture. In one embodiment, an operator may bore out the proximal bone fragment (the fragment closest to the operator) such that sleeve 1008 threads will not engage the walls of the hole. Inserting lagwire 1071 and anchoring head 1009 into the distal bone fragments such that applying a force on lagwire 1071 will compress the bone fragments. The operator may compress the bone fragments with lagwire 1071 and thread threaded sleeve 1008 over lagwire 1071. The operator may thread sleeve 1008 into the distal bone portion to any desired distance.

In accordance with various embodiments, once the sleeve is threaded, the operator may thread cap 1120 over sleeve 1008 until cap 1120 contacts the exterior of the bone and/or another structure such that sleeve 1008 cannot be pulled farther into the bone any substantial distance, due to the bone fragments trying to separate. In another embodiment, cap 1120 may be threaded onto sleeve 1008 before sleeve 1008 is inserted into the bore. In various embodiments, the cap and sleeve may be configured to reduce the bone facture and maintain reduction across the fractured bone fragments. In various embodiments, sleeve 1008 and/or cap 1120 provides improved healing of the fracture and the surrounding tissue.

In accordance with various embodiments, sleeve 1008 may aid in securing a fracture without the support of the wire (or with minimal support). As such, sleeve 1008 may be cannulated for sliding over a wire as described in other embodiments or the sleeve may be a solid wire made of PEEK or other biocompatible materials. In such embodiments, the device will be referred to as a sleeve while still respecting that in the various embodiments it may not be cannulated but may be a solid wire. In various embodiments the sleeve may have various distal tips which enable it to more easily advance through a canal.

In one embodiment, an entry point is created in the bone. A lagwire (i.e. the anchor and wire) is inserted into the entry point and a canal is reamed through a center portion of the bone (see for example FIG. 1F) and across a fracture in the bone (see for example FIG. 4A-4C). As discussed in other embodiments tension may be applied on the lagwire causing the gap at the fracture to be decreased (e.g. lagging the fracture back together). With the fracture reduced, the lagwire may be removed.

Figure 2D:
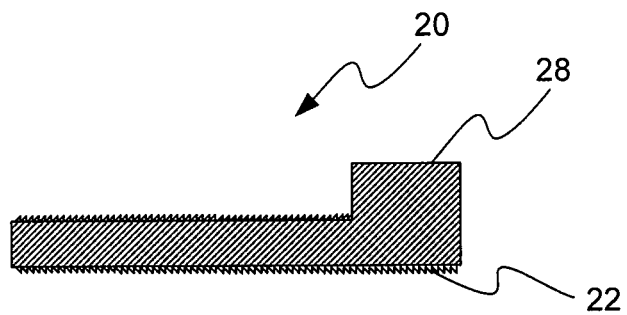
FIG. 2D is a flat cap in accordance with an exemplary embodiment.
Figure 2E:
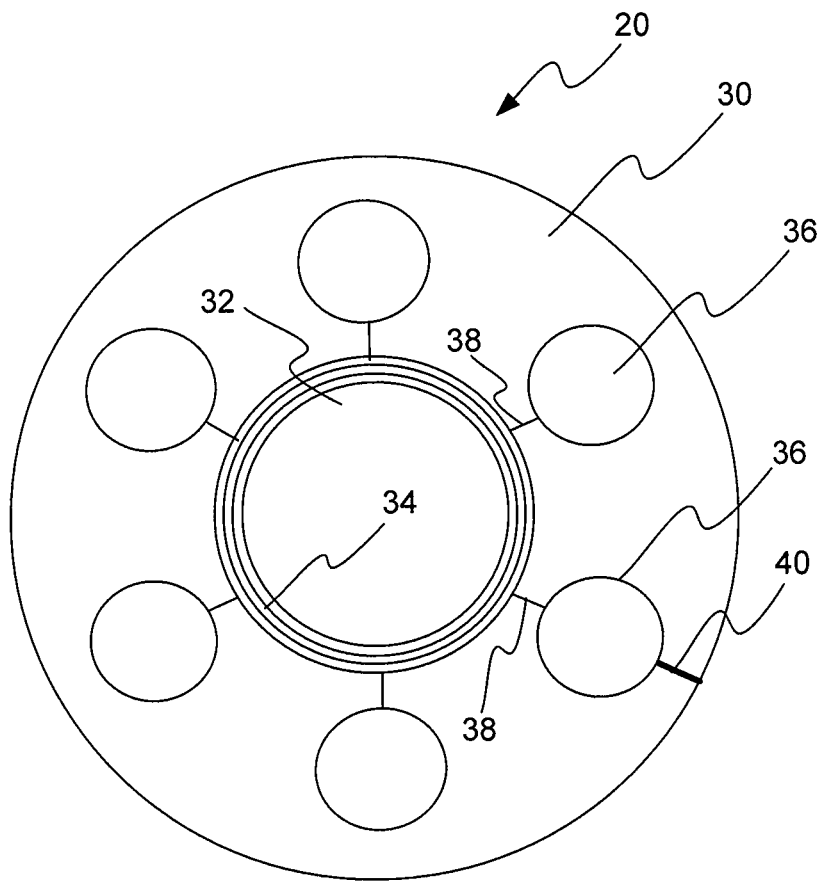
FIG. 2E is a top view of an alternative embodiment of a cap in accordance with an exemplary embodiment.
Figure 2F:
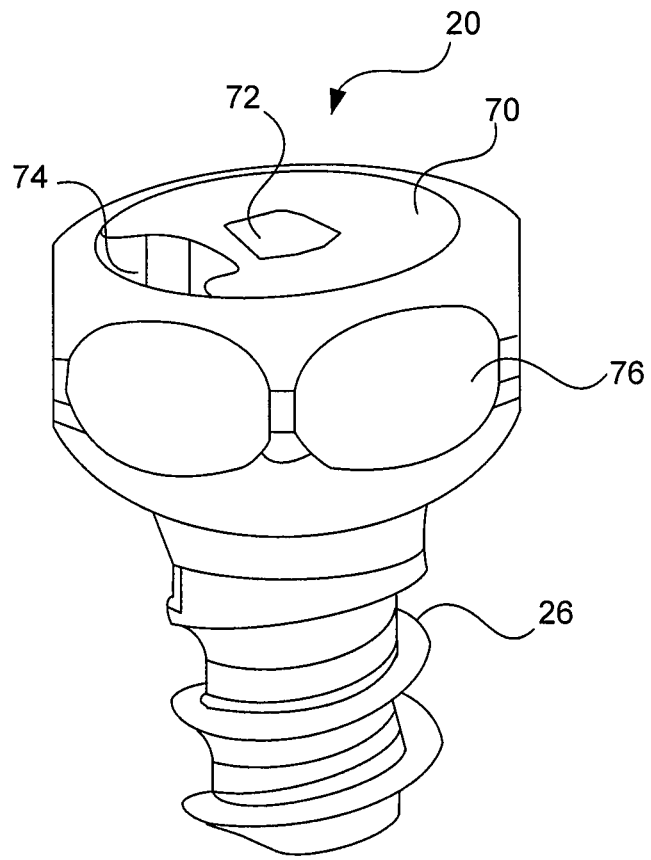
FIG. 2F is a perspective view of another embodiment of a cap in accordance with an exemplary embodiment.
Figure 2G:
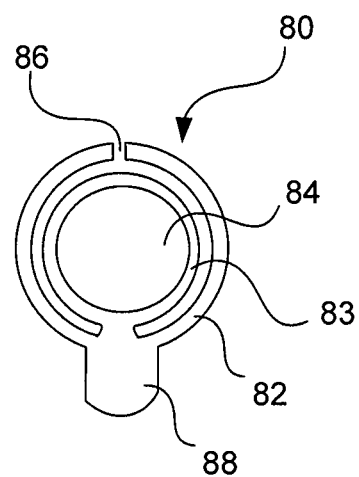
FIG. 2G is a top view of an exemplary spring in accordance with an exemplary embodiment.
Figure 2K:
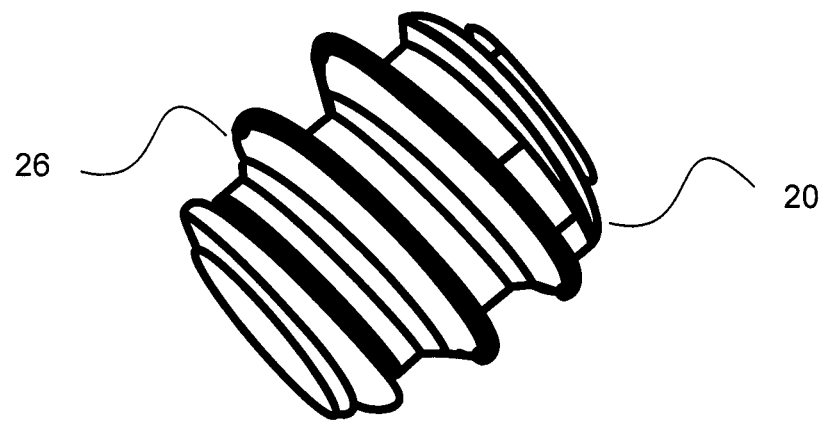
FIG. 2K is a perspective view of an exemplary embodiment of the cap.
Figure 2L:
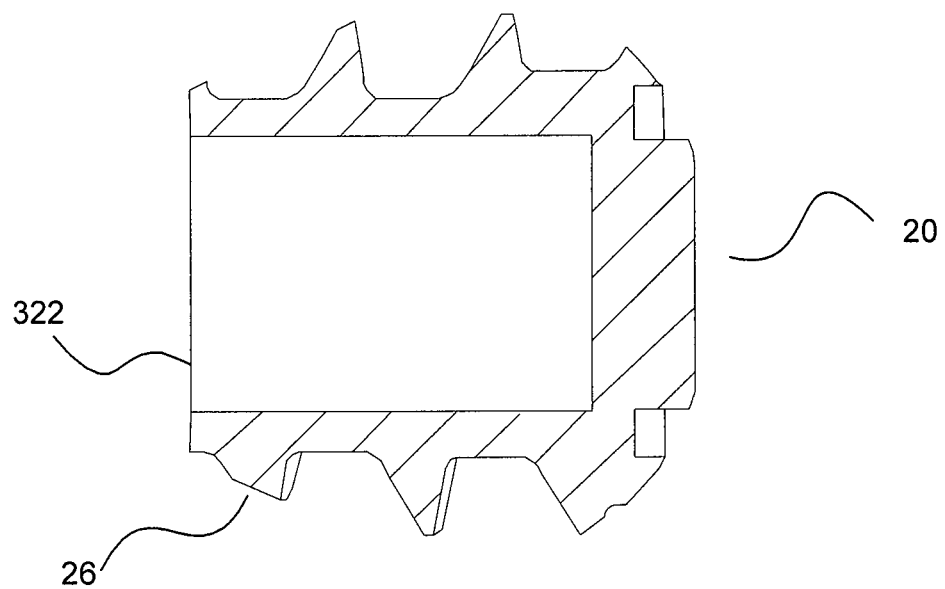
FIG. 2L is a cross section view of the cap shown in FIG. 2K.
Figures 2X, 2Y:
FIG. 2X is an exploded view of the lagwire device.
FIG. 2Y is an assembled view of the lagwire device of FIG. 2X.

With reference to exemplary FIG. 2X and 2Y, and in accordance with another embodiment, the lagwire may be used to ream a canal in the bone with head 1009 and across the fracture but be removed without reducing the fracture. After the canal has been prepared, sleeve 1008 may be inserted into the canal. Sleeve 1008 may be advanced into the canal until the sleeve bridges the fracture in the bone. In various embodiments, the sleeve may have a distal thread 1014 and/or the sleeve may have a proximal thread 1015. In various embodiments, the sleeve may be fully or partially threaded (as previously discussed). The threads allow the sleeve to be threaded into and engage the canal through either a partial length or the entire length of the sleeve. Distal threads 1014 may allow the distal end of the sleeve to be threaded into a distal bone fragment. The proximal end of the sleeve may be retained in the proximal bone fragment using proximal threads 1015.

In various embodiments, the sleeve may be attached to the anchor and sent down a prepared canal as one piece. The sleeve and the lagwire may be used in concert to bridge and/or reduce the bone fracture. In one example, the attachment between the sleeve and the anchor may be a weld. However, the attachment between the sleeve and the anchor may be accomplished in any manner known in the art, such using one or more of adhesive, mechanical attachment (e.g. threaded together, interference fit, etc.), fasteners, etc.

In another embodiment, the proximal bone portion may be over reamed, such that sleeve 1008 does not engage the canal in the proximal and consequently sleeve 1008's movement is not restricted by the canal. However, the sleeve engages in (and the sleeve's movement is restricted by) the distal bone portion where the canal is not over reamed. The sleeve may then be placed in tension by applying a force on the sleeve in the proximal direction, thereby forcing the distal bone portion towards the proximal bone portion. Cap 1120 may then be threaded over the sleeve (e.g., into the canal) in the proximal bone portion. Cap 1120 interior threads may engage sleeve 1008 and cap 1120 outer threads may engage the canal. With the distal portion of the sleeve retained in the distal bone portion and the proximal portion of the sleeve retained in the proximal bone portion by cap 1120, the sleeve tension may be fully or partially maintained.

In various other embodiments, the sleeve may be smooth, threaded, and/or have any surface features, composition or textures. Furthermore, the sleeve may be held in the various bone fragments by other devices engaging the sleeve from a perpendicular direction, after it has been inserted into the various bone portions. For example, posts may be attached to the sides of the sleeve. In one embodiment, ultrasonic welding may be utilized to hold the posts in the side of the sleeve. In accordance with various embodiments, ultrasonic welding may be utilized on any component described herein to fasten other components, devices or features thereto.

With reference to exemplary FIG. 2Z.1-5 and in accordance with another embodiment, sleeve 1008 may comprise one or more coiled and/or helical fibers. Such a configuration may also be referred to as hollow helical spring sleeve. For example, as illustrated in exemplary FIG. 2Z.1 and 2Z.2, four fibers 1111, 1112, 1113, and 1114 may be interwoven to form sleeve 1008. In one example, the fibers may be interwoven such that each individual coil from each fiber is separated by coils from other interwoven fibers, as shown in FIG. 2Z where one coil is fiber 1111, then the next adjacent coil may be fiber 1113, then the next adjacent coil may be fiber 1112, and the next adjacent coil may be fiber 1114. While in the illustrated example four fibers are used, in various other embodiments, any number of fibers can be used, such as a single coil, two entwined coils, three entwined coils, etc. For example, with reference to exemplary FIG. 2Z.3-2Z.5 six fibers may be incorporated in to the sleeve. In this example additional fibers 1115 and 1116 are incorporated.

In another embodiment, the interwoven fibers may comprise multiple layers. For example, four fibers may be woven as indicated above forming a first layer and another set of four fibers with a larger diameter coil may be interwoven over the first layer. In may be noted that any number of fibers and or layers may be incorporated in the weaving process.

In accordance with various embodiments, each fiber may have different a cross section, size and/or shape. In one example, the fibers may have a shape that is square cross section. Or in another example, in a sleeve wherein two fibers form the sleeve, one fiber may have a small diameter and the other fiber may have a larger diameter. (see, for example, fiber 1111 in FIG. 2Z compared to fiber 1112 in FIG. 2Z). When interweaving the two fibers, the larger diameter cross section may extend outward with the smaller diameter cross section coils separating the larger diameter coils. One effect is a solid sleeve with the appearance of threads formed by the large cross section coils. In one example, the outer diameter of the larger coil may be about 4 mm, and the outer diameter of the smaller coil may be about 3.5 mm. Whereas, the fiber of the larger coil may be about 0.8 mm and the fiber diameter of the smaller coil may be 0.6 mm.

In accordance with various embodiments, the shape of the fiber cross sections can be designed to match a thread profile on any surface on the outside of the coil/helix. The fiber cross section may be further configured such that the surface between each of the coils of each fiber is optimized to securely nest and/or contact with the coils from other fibers which are interwoven together. For example, a first fiber with a large cross section may have two angled surfaces on the outside of the coil which matches a thread profile. The first fiber may have a thread like edge that is always maintained at a normal direction to the coil rotation That is, a thread edge that is pointing out from the axis of rotation to produce a consistent thread pitch and shape. In various embodiments, a second fiber may have a flat surface on the outside of the coil, but have a top and bottom surface configured to mate with and/or engage with the larger cross section of the coil on the first fiber, allowing the two fibers to be interwoven creating a substantially solid single sleeve.

In various embodiments, the threads of the sleeve may be controlled by the number and diameter of the fibers. For example, six fibers may be incorporated in to the sleeve. In various examples three fibers may be a first diameter and/or cross section and three fibers may be a second diameter and/or cross section. In various other examples, the sleeve may include two fibers of a first diameter (which may be larger) and four fibers of a second diameter which (which may be smaller.) This may produce a thread with the same pitch, however it would have an effective thread profile of twice the width.

In accordance with various embodiments, fibers may be constructed from a variety of materials such as stainless steel, aluminum, PEEK titanium, nitinol and/or other biocompatible materials. In accordance with various embodiments, the fibers may be commonly acquired structures such as springs. For example springs of different cross sections may be threaded together to form the sleeve. In accordance with various embodiments, a manufacturing method of the sleeve may comprise wrapping the fibers around a constant diameter mandrel that acts as the core of the coil. The coil may then be slipped off the mandrel and finished. In accordance with various embodiments, coils may be produced by high speed fine machining of tube material. The cutters may break through the tube into the center area and free the fibers to move.

In accordance with one exemplary embodiment, a lagwire system may be used to deliver treatment to a desired location. The treatment delivered by the lagwire system may comprise any composition, device or structure that will facilitate the fixation and/or provide support to bones. For example, the treatment may comprise medications (such as bone growth stimulation drugs or structures), adhesives, implants, fasteners, ligaments, tendons, and suturing materials. In one embodiment, a bondable material may be delivered to the bone to facilitate the joining of bone fragments. For example, the materials disclosed in U.S. Pat. No. 7,217,290 entitled "SURGICAL DEVICES CONTAINING A HEAT BONDABLE MATERIAL WITH A THERAPEUTIC AGENT," (the '290 patent) which is herein incorporated by reference in its entirety, may be delivered to a region of interest using the lagwire system disclosed herein.

A desired location may be any position on or within one or more bones. It will be understood that the present system and method may be used in connection with any type of bone, such as a clavicle, pelvis, humerus, tibia, ulna, and/or the like.

In one embodiment, a lagwire system may be used to deliver treatment to the interior of a bone. For example, the lagwire system may be used deliver treatment via an intermedullary canal.

Figure 1Q:
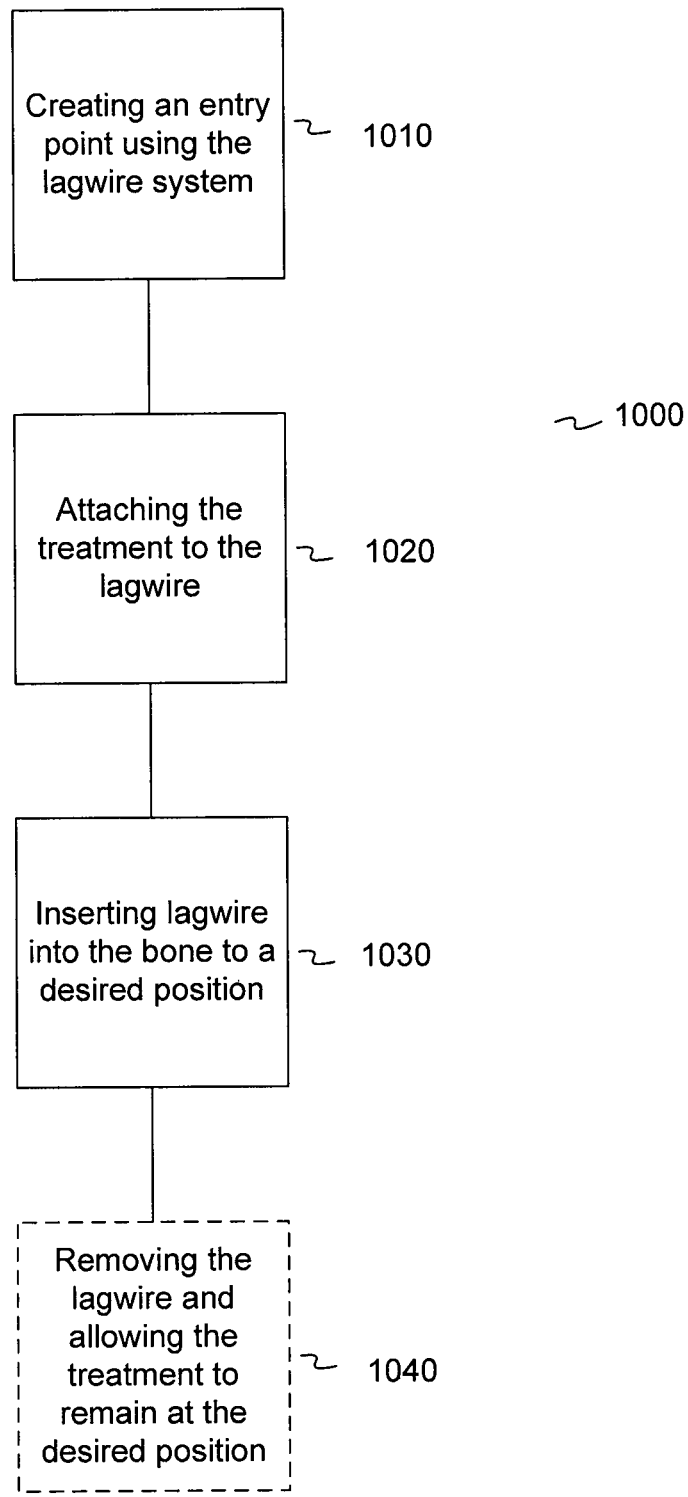
FIG. 1Q illustrates an exemplary method of using the lagwire system to deliver treatment to a desired location.

As shown in FIG. 1Q, an exemplary method 1000 may comprise the steps of: creating an entry point into the bone using the lagwire system (this may be accomplished manually or under power) (Step 1010), attaching the treatment to the lagwire (1020), inserting the lagwire into the bone, such as through the intermedullary canal, to a desired position (Step 1030). Method 1000 may also include the step of removing the lagwire and allowing the treatment to remain at the desired position (1040). In other embodiments, the lagwire may be left within the bone. In some embodiments, an optimal entry point for the lagwire is selected based upon the unique size and shape of the bone. As discussed herein, the lagwire may be suitably flexible to permit the device to travel through linear or non-linear canals.

In one embodiment, the treatment (such as liquid and/or gel medication) may be delivered through the center of the tubular or threaded sleeve. In another embodiment, the sleeve may be the treatment itself. In another embodiment, the wire and/or sleeve may transport and/or deliver the treatment to the targeted location.

In various embodiments, the lagwire, sleeve, and/or cap may be used to transmit various frequencies of vibrations to targeted portions of the bone to stimulate or otherwise influence bone growth. In one example the vibrations may be ultrasonic.

The treatment may be attached to the lagwire in any number of ways. In one embodiment, the treatment may be configured as a sleeve that can be inserted over the lagwire. For example, a sleeve comprising a heat-bondable material, such as PEEK or a material disclosed in the '290 patent, may be delivered to a region of interest using the lagwire system. Treatment material may also be inserted into the bone at various locations and angles so as to contact the sleeve comprised of the treatment material located within the canal. Heat or other activating means may then be applied to join the treatment material, thereby creating additional support for the bone.

In various embodiments, a lagwire system which permits movement of the first object relative to the object during treatment may be desirable. For example, in anterior cruciate ligament (ACL) repair, it may be desirable to allow movement of the femur relative to the tibia to permit the knee to function normally. As such, in various exemplary embodiments, the lagwire system may comprise a filament portion which permits movement of a first bone portion relative to a second bone portion. The filament may be any material that permits the desired amount of movement and flexibility. For example, the filament may be one or more of fasteners, ligaments, tendons, and suturing materials (including natural and synthetic structures thereof). Moreover, the filament may be substantially flexible or inflexible and may comprise single or multi-thread materials.

Figure 1R:
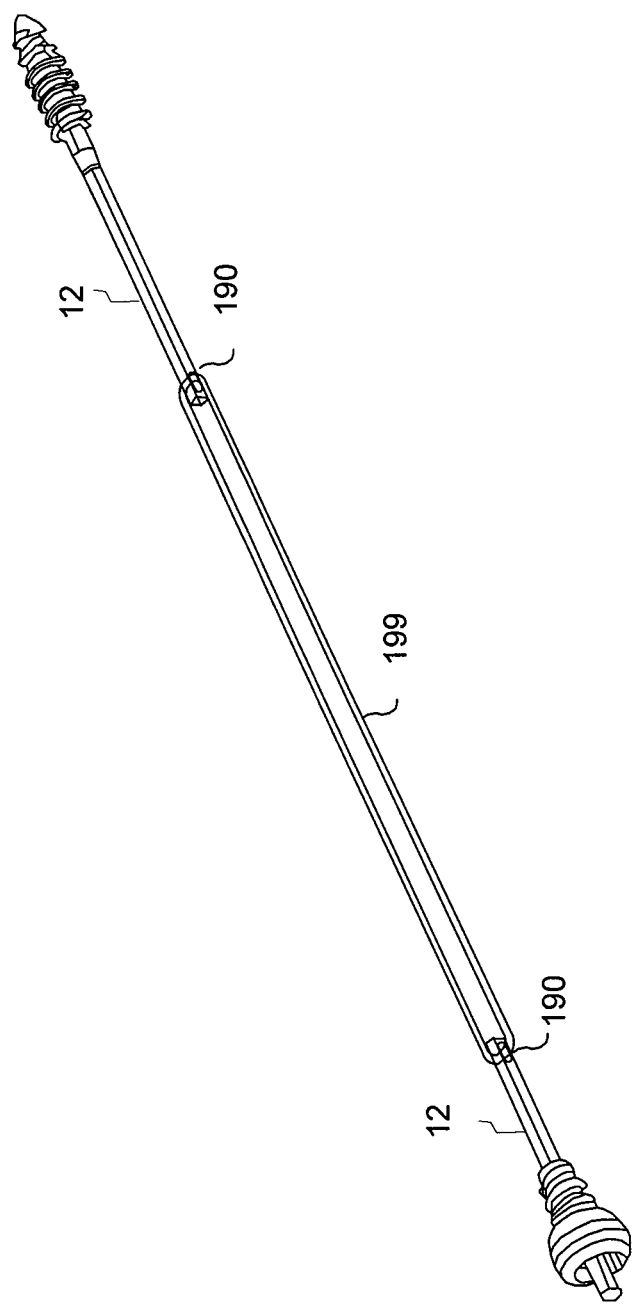
FIG. 1R illustrates an exemplary embodiment of a lagwire system comprising eyelets to facilitate coupling of a treatment to the lagwire.

For example, as illustrated in FIG. 1R, lagwire 12 may comprise eyelets 190 suitable to couple filament 199 (shown herein as a suture thread), to lagwire 12. The eyelets may be located at any position in the lagwire system and the filament may be any desired length. Although the attachment means is illustrated herein as eyelets, it will be understood that the attachment means may comprise any device, structure or component suitable to attach the filament to the lagwire.

An exemplary method includes: providing a lagwire system comprising: (a) an anchor component having a planar surface, threads and a cutting surface having a pointed angle connected to a flexible wire having a filament; (b) inserting the anchor component into a first object using an automatic or manual rotating device, such as a drill; (c) maneuvering the lagwire system through the first object; and, (d) anchoring the anchor component into a second object. The method may further comprise inserting a flexible or inflexible tubular sleeve over the flexible wire.

Cap 20 is any device suitably configured to maintain or increase the pressure between the surfaces of pathology by limiting wire 12 movement. As shown in FIGS. 2A-2E, exemplary caps 20 may include various configurations, materials, shapes and/or sizes. In one embodiment, and as shown in FIG. 2A, cap 20 includes an inverse interface component 22 relative to wire 12 interface component such that cap 20 is restricted from backwards translation after cap 20 is inserted over wire 12. In one embodiment, the interface component 22 on cap 20 is located at least on the inside surface of the cap and includes a saw tooth pattern with the same or similar pitch as the saw tooth on wire 12. This configuration also allows cap 20 to slide along wire 12 without the need for spinning cap 20 which is important because time is of the essence in a medical procedure and spinning the cap down a sufficiently long length of wire would be very time-consuming. Examples of cap 20 include a screw cap 20, flat cap 20 and a quick cap 20. As shown in FIG. 2C, screw cap 20 is configured with teeth 22, cutting threads 24 and/or mating threads 26 on the outside surface to facilitate rotating cap 20 into the cortex to, for example, fix surgical plates against certain pathology. However, cutting threads 24 may not be needed on any of the caps because cutting threads 6 of anchor component 2 may have already tapped the threads on the inside surface of the bone, so the teeth 22 or mating threads 26 alone can simply rotatably engage the threads formed from cutting threads 6 and provide sufficient friction to secure the cap in the bone. As shown in FIG. 2D, flat cap 20 may include teeth 22, cutting threads 24 and/or mating threads 26 on the outside surface to facilitate rotating cap 20 into the cortex, but it also is configured with a flat top surface 28 to allow cap 20 to be inserted into the cortex such that the flat top surface 28 of cap 20 does not substantially protrude from the cortex surface. As best shown in FIG. 2A, for example, the quick cap 20 or any other cap may be configured with only the interface component on the inside surface, thereby allowing for quick and easy assembly.

With reference to FIG. 2E, in one embodiment, cap 20 is configured as a planar disk 30 with a center hole 32, wherein the center hole 32 includes an interface component 34 on its inner circumference surface. In an exemplary embodiment, the pitch of the saw tooth interface component is about 0.25 mm-0.5 mm. The planar disk 30 may also include any configuration for facilitating expansion of the disk 36 while sliding down wire 12. The configurations may include, for example, a cut 38 or a hole 36 in the planar disk 30. The planar disk may include multiple holes or cuts spaced over the planar surface. One or more of the additional holes 36 may also be connected to a cut 38 in the planar surface that extends to the center hole 32. One or more of the holes 36 may also be connected to a cut 40 in the planar surface that extends to the outside edge of the planar surface. In one embodiment, six additional holes 36 are evenly spaced around the planar surface with each hole 36 connected to a cut 38 which extends to the center hole, while one hole 36 also includes a cut 40 that extends to the outside edge of the planar surface.

The planar disk may also set inside a shallow cup device, wherein the circumference of the cup is slightly larger than the circumference of the planar ring in order to allow expansion of the ring. Moreover, a spring, or any other device suitably configured to apply pressure to cap 20, is placed between the planar ring and the cup device. In one embodiment, a bellville spring is used to apply pressure to the cap 20. The spring is configured to provide force on wire 12 after resorption. During the healing process, cartilage forms at the fracture and the cartilage compresses, so bone resorption typically occurs at the location of the fracture. When force on the lagwire is released due to bone resorption during healing, in one embodiment, cap 20 allows for auto tightening of the lagwire because micro-motions or vibrations will often cause cap interface device 22 to click down another notch on the inverse interface device of the wire 12.

Another embodiment of a cap 20 is shown in FIG. 2F. As discussed above, cap 20 fits over one end of wire 12, such that cap 20 permits travel of cap 20 in one direction (e.g., distal travel with respect to the wire, toward the bone), but resists travel of cap 20 in the other direction (e.g., proximal travel with respect to the wire, away from the bone). In exemplary embodiments, cap 20 includes cutting threads 26, cover 70, a spring 80 and substantially flat surfaces 76 around the circumference of cap 20 to facilitate griping and/or turning cap 20. Cap 20 may be configured with a wider upper section which includes flat surfaces 76 around its circumference, and a tapered lower section with a gradually reducing diameter. Cutting threads 26 extend from the lower section. Cap 20 may include different thread configurations, lengths, diameters, pitches and the like to facilitate insertion into different types of bone or other structures (e.g., cortical bone, cancellous bone, etc). Cover 70 may be integral with cap 20, or may be a separate component which is permanently or temporarily set in, or affixed to, cap 20.

In one embodiment, cover 70 includes an opening 72 (e.g., in center of cover 70) which receives wire 12 and an inlet 74 which is configured to receive a component of extractor tool 90. Other embodiments of caps are disclosed in U.S. application Ser. No. 11/952,413, filed on Dec. 7, 2007 and entitled "SYSTEM AND METHOD FOR A CAP USED IN THE FIXATION OF BONE FRACTURES," which is herein incorporated by reference in its entirety.

In one embodiment, tension spring 80 is set inside cap 20. In one embodiment, and with reference to FIG. 2G, tension spring 20 sits within cap 20 below cover 70; is circular;

includes opening 84 (e.g., in center of circular ring) which receives wire 12; includes an outer ring 82 and an inner ring 83; includes a cut into, or non-connecting portion 86 of, outer ring 82 and/or inner ring 83; and/or includes a tab 88 which extends outward from outer ring 82. Outer ring 82 and an inner ring 83 may be one integrated ring, or two or more separate rings, which may not be connected, or may be connected in any manner.

At least a portion of inner ring 83 (or any portion of inner circumference of tension spring 80) provides greater friction against wire 12 one way (e.g., when the cap is pulled proximal, away from the bone). The friction is asserted against wire 12 because cover 70 impacts tab 88, so tab 88 forces tension spring 80 to flex, torque and/or tilt (e.g., 15 degrees) opening 84, thereby causing at least a portion of inner ring 83 to assert friction against at least a portion of wire 12. When cap 20 is pushed the other way (e.g., when the cap is pushed distal, toward the bone, using extractor 90), tab 88 is forced away from cover 70 and does not tilt, so it does not engage any surface, and the wire is able to translate, with minimal or no friction, through the central opening in the tension spring.

Another embodiment of a cap 20 is shown in FIGS. 2H, 2I, and 2J. FIG. 2H shows and exploded view of an example of the cap 20 with a cover or recessed nut 70, an angle or lever clutch 300, a tension spring 80, and a body 302. When assembled, as shown in the perspective view of FIG. 2I or cross section view of 2J, the tension spring 80 resides within a chamber of the body 302, between the body 302 and the cover 70. The locking lever clutch 70 also resides between the body 302 and the cover 70, and is in movable contact with the spring 80. The spring 80 is a flat spring washer that applies a preloaded force to the lever clutch 300, biasing the lever clutch 300 to skew to a plane that is not parallel with the plane of the spring 80. In its skewed state, the lever clutch 300 includes defines a hole 304 along a central axis 306 that is not coaxial with a central axis 308 of the cap 20, and frictional edges 310 defining a portion of the hole 304 are forced into frictional contact with one or more flat or rounded outer surfaces of a wire 12 running along the axis 308 of the cap.

The tension spring 80 may, for example, be formed of a relatively thin layer of nitinol or another resilient material. The lever clutch 300 may, for example, be formed of a thicker layer of stainless steel or titanium. The relatively thin layer of the tension spring 80 occupies minimal space within the chamber of the body 302, minimizing the overall size of the cap 20. The relatively thick layer of the lever clutch 300 provides greater surface area and strength to maximize stable and strong frictional contact and lock between the frictional edges 310 and the outer surface of the wire 12. In an exemplary embodiment, the lever clutch 300 and spring 80 are either attached to each other or formed as a single structure and may be formed of identical or varying materials and thicknesses.

The frictional edges 310 permit distal movement of the cap 20 with respect to the wire 12 as the wire 12 moves through the central axis 308 of the cap 20 and forces or biases the locking lever clutch 300 to move upwards towards the cover 70, towards a plane that is closer to parallel with the plane of the spring 80, and in an orientation that permits the body of the wire 12 to move through the hole 304 with less frictional contact against the frictional edges 310. In contrast, the frictional edges 310 resist proximal movement of the cap 20 with respect to the wire 12 as the wire 12 moves through the central axis 308 of the cap 20 and forces or biases the locking lever clutch 300 to move downwards away from the cover 70, towards a plane that is closer to perpendicular with the plane of the spring 80, and in an orientation that resists movement of the body of the wire 12 through the hole 304 as the frictional edges 310 are forced against and in increasing frictional contact with the outer surface of the body of the wire 12.

The embodiment of a cap 20 described with reference to FIGS. 2H, 2I, and 2J can be unlocked during or after initial implantation to make adjustments to, replace, or remove any or all of the system 1. To unlock the lever clutch 300 of the cap 20, a user may manually, or by means of a special hook-like tool, raise a handle 312 of the clutch 300, for example, by exerting force on a lower edge 314 of the handle 312 in a direction that releases the friction edges 310 from their locking position with respect to the outer surface of the wire 12.

In some situations, it may be desirable to prevent the first and second bone portions from separating as well as further compressing during treatment. For example, if the bone is brittle, angled or contoured, further compression may damage the bone fragments and impede recovery. As such, in various embodiments, a cap may be any device which is operable to lock onto the wire so as to prevent further backward or forward translation of the cap relative to the wire. For example, the interior of the cap may comprise one or more protrusions (e.g. teeth and/or fingers) or other means operable to clamp, crimp and/or squeeze the wire to prevent further movement relative to the cap. In an embodiment, the interior of the cap is tapered such that when the cap is advanced along the wire, the tapered portion clamps down on (or squeezes) the wire until further movement of the cap is impeded. The cap may also include slits or cut-out areas which allow the surface of the cap to flex or bend.

In another embodiment, the cap may be configured to prevent the sleeve or wire from backing out of the bone, without the cap locking onto the wire or support sleeve. Referring to FIG. 2L, in an exemplary embodiment, the cap 20 comprises threads 26 and a blind hole 322 wherein blind hole 322 is sized to receive the wire 171 and/or the supporting sleeve 141. As an example, blind hole 322 can be a concave cavity or opening, specific depth hole, or a hole with other features such as a counterbore. In this embodiment, the cap may not have a through hole. Therefore, the wire and support sleeve may not pass through the cap. Instead, the cap may be configured to prevent the wire and support sleeve from backing out of the bone canal. The cap may be screwed into the bone canal (wherein the wire and sleeve occupy the bone canal), after the break has been properly anchored as discussed previously. By screwing (e.g., rotating) the cap into the bone such that the wire and supporting sleeve rest inside of the cap blind hole 322, (see FIG. 2N and 2O) the wire and support sleeve are partially or fully prevented from backing out of the bone canal (or only minimally back out of the bone canal). It may also be noted that this embodiment may function without the presence of threaded sleeve 192.

In various other embodiments, the cap may not have a blind hole, but instead acts as a plug when screwed into the bone canal. In such an embodiment, the cap may be screwed into the bone canal an optimal distance such that it does not apply excessive pressure against the wire and sleeve, but also far enough so the wire and sleeve are partially or fully prevented from backing out of the bone canal.

In various other embodiments and illustrated in FIG. 2U, cap 1120 may have internal threads configured to mate with and/or thread onto a threaded sleeve. In another embodiment, cap 1120 may have internal cutting threads configured to cut onto the outside surface of the tubular sleeve. In another embodiment, cap 1120 may have external threads configured for threading into a retaining cap in the bone. By engaging the bone (as discussed herein) and retaining sleeve 1008, cap 1120 may constrain the sleeve in relation to the entry point into the bone.

In various other embodiments, the cap and the threaded (and/or tubular) sleeve may engage one with the other any way discussed herein, in the incorporated references, or known in the art. For example, the cap may employ a clutch mechanism to engage the threaded or tubular sleeve. In another example, the cap may employ a wedge mechanism to engage the threaded or tubular sleeve.

Figure 5A:
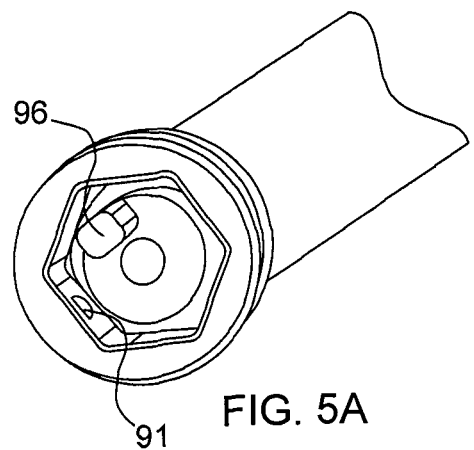
FIG. 5A is an exemplary head of the extractor of FIG. 5B in accordance with an exemplary embodiment.
Figure 5B:
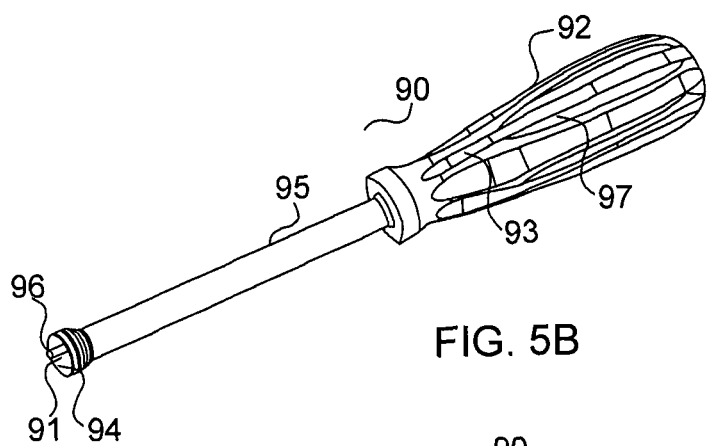
FIG. 5B is an exemplary extractor in accordance with an exemplary embodiment.

Extractor/Driver 90, with reference to FIGS. 5A and 5B, includes any device suitably configured to insert and/or extract cap 20. In one embodiment, extractor 90 includes one or more ball bearings 91, shaft 95, shaft end 93, handle 92 which receives shaft end 93, tip sleeve 94, tip 96, and/or spring 97. Tip 96 may be the end of a long rod which extends upward into handle 92. Spring 97 applies pressure against the upper end of the rod that emanates from tip 96, thereby asserting a load against tip 96. Tip 96 is thus configured to be received into inlet 74 of cap 20 and the spring-load maintains tip 96 in inlet 74. Tip sleeve 94 is configured to receive cap 20 to also facilitate rotation and/or translation of cap 20. Tip 96 is mounted on a disc such that it allows tip sleeve 94 to more fully receive cap 20. The disc also rotates such that extractor 90 may rotate around cap 20, with minimal or no movement of tip 96. Ball bearings 91 are configured to facilitate rotation of tip sleeve 94 around outer surface of cap 20.

Figure 5C:
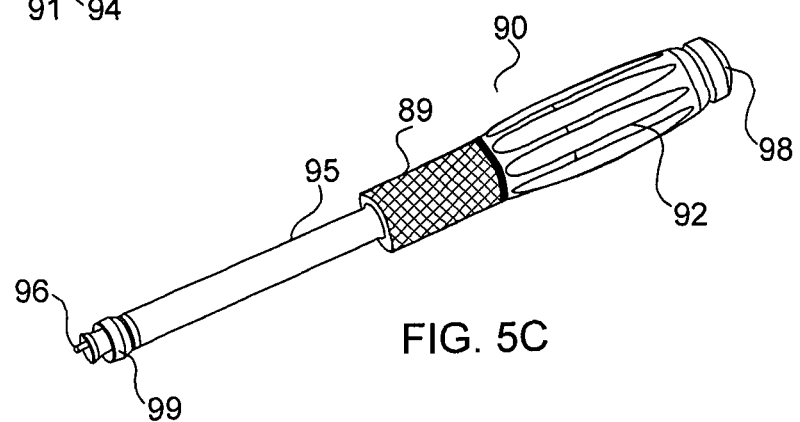
FIG. 5C is another embodiment of an exemplary extractor in accordance with an exemplary embodiment.

Another embodiment of extractor/driver 90 is shown in FIG. 5C. In this alternative embodiment, the rod may have a first end which includes tip 96, and a second end 98 which may exit handle 92 such that the user may apply pressure to the second end 98 of the rod, thereby similarly applying pressure and a load against tip 96. Exit handle 92 also rotates such that it enables rotation of tip 96 which allows the user to rotate tip 96 until tip 96 mates with the inlet in cap 20. In another embodiment, collet sleeve 99 is attached to collet advancing handle 89. Collet advancing handle 89 includes a threaded inner surface which is configured to advance shaft 95, and thus, advance collet sleeve 99 forward over cap 20 to facilitate grasping of cap 20 for removal of cap 20.

Figure 3A:
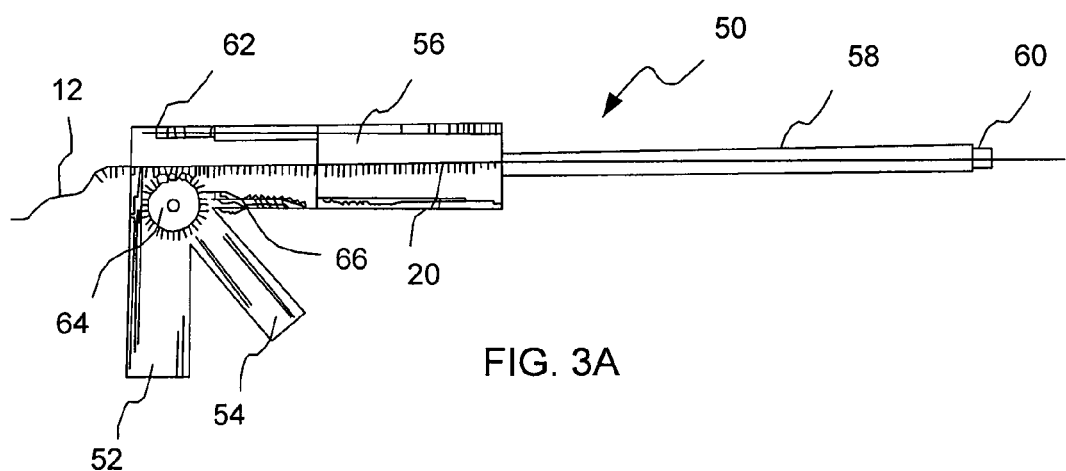
FIG. 3A is a tensioner in accordance with an exemplary embodiment.

A tensioner 50 may also be used in conjunction with various embodiments. With respect to FIG. 3A, tensioner 50 is any device suitably configured to insert a cap 20 into an object and/or provide tension to a wire 12. In one embodiment, tensioner 50 increases the pressure between the surfaces of pathology by providing force to a wire 12 while the anchor component 2 of wire 12 is fixed into a bone or far cortex. In an exemplary embodiment, tensioner 50 includes a handle 52 with a hand trigger 54, wherein the handle 52 supports a rotatable barrel 56 which mates with a cylindrical rod 58. Cylindrical rod 58 may be cannulated to receive wire 12 and/or have a driver 60 (e.g., hex, phillips, screw, allen and/or the like) at its distal end for mating with the tool attachment 10 of anchor component 2. The barrel 56 may be rotated manually or automatically in order to rotate the driver 60 into the object (e.g., bone or cortex). In one embodiment, tensioner 50 includes a means for exerting a force on wire 12, such as, for example, internal gears 64, wherein the gears 64 include an interface component 66 (e.g., saw tooth) which mate with the inverse sawtooth 20 on wire 12. By pivoting the hand trigger 54, the internal gears are rotated such that the gears cause wire 12 to translate out the back end 62 of the tensioner 50, thereby exerting force on wire 12 which is fixed at its distal end. The tensioner 50 may also include a gauge type device or any other device which is suitably configured to measure and/or display the tension exerted on wire 12.

Figure 3B:
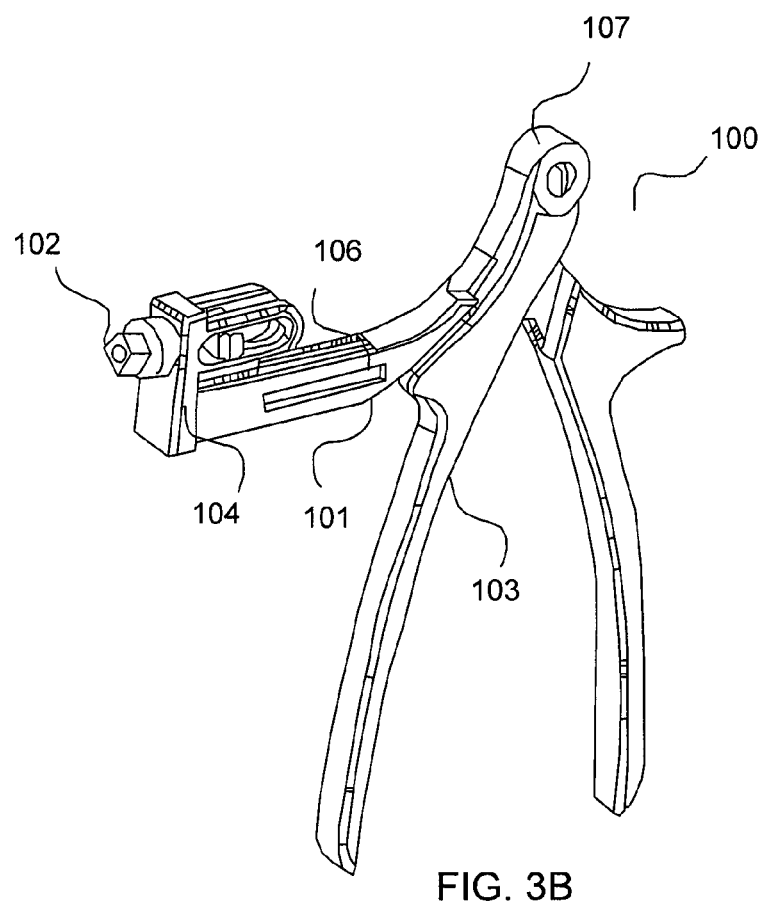
FIG. 3B is another embodiment of a tensioner in accordance with an exemplary embodiment.

Another embodiment of a tensioner (e.g., tensioner 101) is shown in FIG. 3B. In one embodiment, tensioner 100 includes a base 101, a DVR connect component 102, a handle 103, a lock 104, and/or a spring link 106. Tensioner 100 is configured to accept multiple size wires and may include an indicator to show the amount of tension being applied. Tensioner 101 is also configured such that extractor 90 may clip into tensioner 101. Other embodiments of tensioners are disclosed in U.S. application Ser. No. 12/104,328, filed on Apr. 16, 2008 and entitled "TENSIONING SYSTEM AND METHOD FOR THE FIXATION OF BONE FRACTURES," which is herein incorporated by reference in its entirety.

Figure 6:
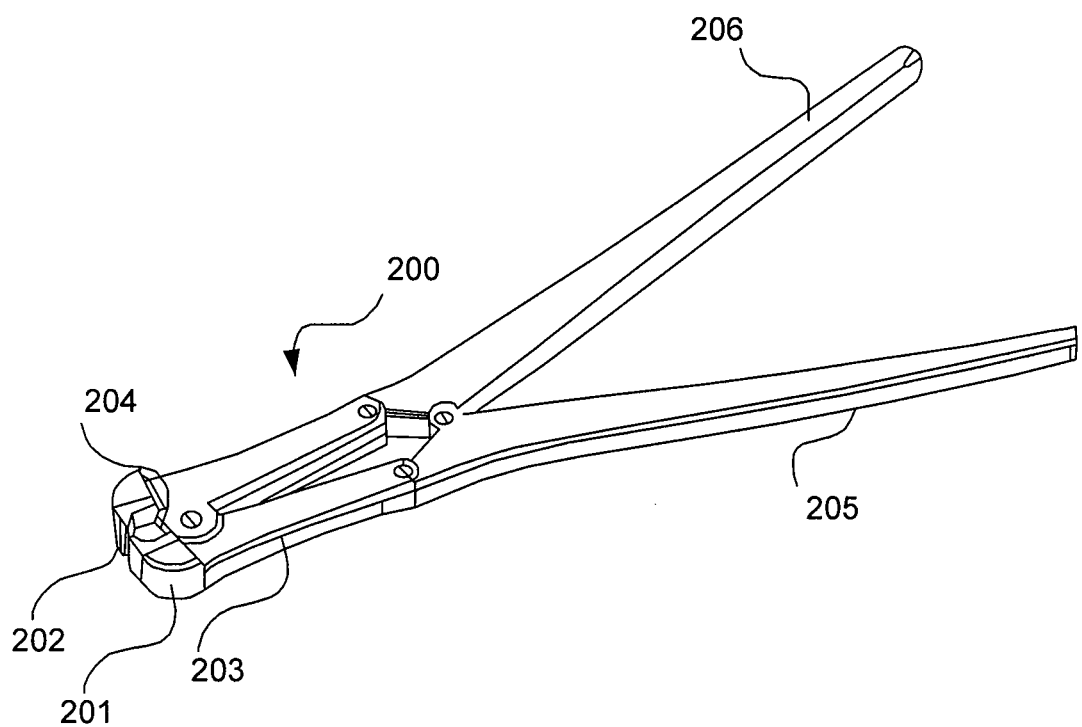
FIG. 6 is an exemplary cutter in accordance with an exemplary embodiment.

After tensioning wire 12 to the desired tension, wire 12 may be cut, broken or shortened using any known device or method. With reference to FIG. 6, cutter 200 may be used. Cutter 200, in one embodiment, includes insert left 201, insert right 202, jaw left 203, jaw right 204, cutter left 205, and cutter right 206. Cutter 200 includes a cutting surface that extends beyond the main body of cutter 200 such that the wire may be cut from various angles.

The various components discussed herein can be suitably configured to perform the following method, wherein the steps can be performed in any order and any individual step is not necessary to the method. In an exemplary embodiment, a cannulated lagwire driver is suitably attached to a surgical drill, such that the drill allows for automatic rotation of the driver. The wire 12 of lagwire system 1 is placed into the channel of the driver such that the end of the driver encompasses or is received into driver head 10 of anchor component 2, thereby allowing wire 12 to be drilled into the bone. In one embodiment, anchor component 2 is configured with a hex head as the driver head 10 such that the driver suitably mates to the hex head. The anchor component 2 and wire 12 are then drilled into the bone to a desired depth using the automatic surgical drill (or any other manual or automatic device for rotating anchor component 2). Specifically, drill tip 4 of anchor component 2 facilitates the drilling of a pilot hole, wherein the proximal cutting threads 6 tap the bone for threading the inner surface of the hole, then the proximal mating threads 8 rotationally mate with the newly created threaded surface, thereby temporarily attaching the anchor component 2 into the cortex of the bone.

After attaching the anchor component 2 to the bone, the surgical drill is removed and a cap 20 is threaded onto the proximal end 14 of wire 12. Cap 20 is then translated distally along wire 12 until cap 20 contacts the bone or other desired pathology. In one embodiment, a lagwire tensioner is used to exert tension on the lagwire. In another embodiment, a lagwire tensioner 50 may be used to force or seat cap 20 into the bone surface or any other desired position. The hex head 60 of the tensioner 50 may be used to screw cap 20 into the bone surface. In another embodiment, the lagwire tensioner 50 exerts tension on the lagwire 12 up to a desired tension which may be read from a gauge communicating with the tensioner.

After positioning the lagwire device 1 and applying the appropriate amount of tension, in one embodiment, the excess wire 12 may be suitably removed by, for example, a wire cutter or any other suitable device. In another embodiment, a crimp type device may be placed on wire 12 to also help maintain tension. The crimp may include a clamp type device, bending the existing wire 12, screwing a nut onto the end of wire 12 and/or the like. The crimp may be placed on wire 12 after cap 20 is set in place, for example, in order to crimp other end pieces together. The tensioner 50 may also be used to reverse screw cap 20 in order to remove a wire 12 out of the bone. Moreover, in a situation where anchor component 2 strips out of the bone (for example, when the bone is of poor quality), the present system allows the lagwire to be pushed through the opposite side of the bone and through the skin such that the anchor component 2 of wire 12 can be suitably removed (e.g., cut off) and a cap 20 can be placed onto that end of the lagwire, thereby resulting in better purchase (e.g., quality of fixation) of the bone.

Figure 4D:
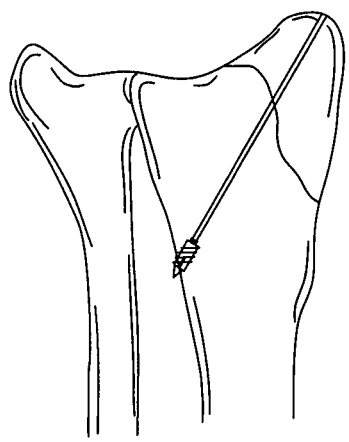
Figure 4E:
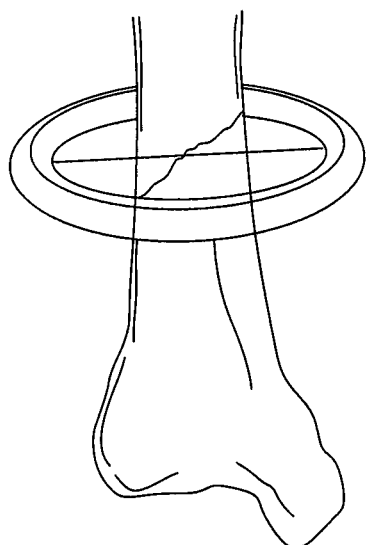
FIG. 4E is a fixation of a bone fracture by inserting the lagwire through the entire limb to facilitate attaching an external fixation device to the limb in accordance with an exemplary embodiment.
Figure 4F:
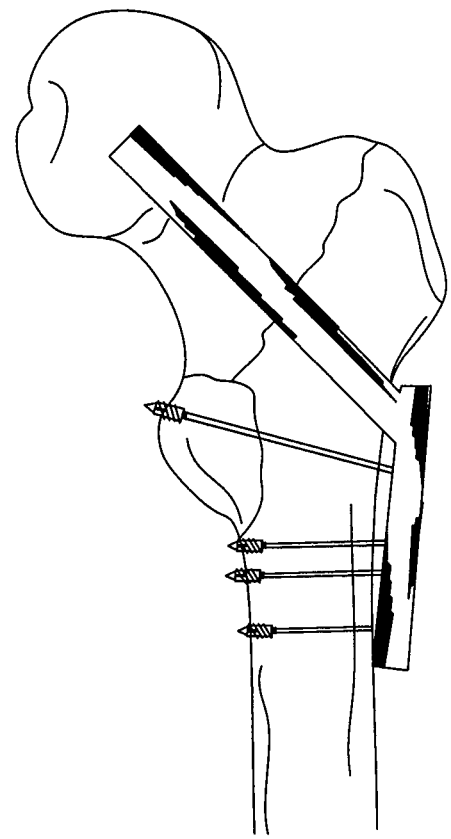
FIGS. 4F-4G is a fixation of a bone fracture by inserting the lagwire through the entire limb to facilitate holding a plate to the bone to help fix certain types of fractures in accordance with an exemplary embodiment.
Figure 4G:
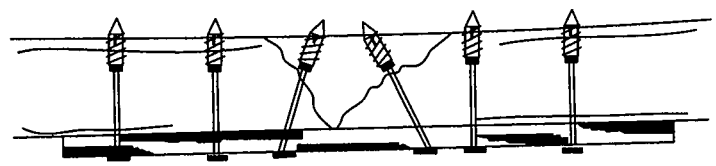

With respect to FIGS. 4A-4G, the lagwire system discussed herein can be used for the fixation of various types of bone fractures. FIG. 4A shows the use for an exemplary fixation of a bone fracture or break. FIGS. 4B-4D show the use for an exemplary fixation of fractures of certain portions of bones. Moreover, as shown in exemplary FIGS. 4F and 4G, the lagwire system 1 may also be used in a similar manner discussed herein in order to assist in holding a plate to the bone to help fix certain types of fractures. In other types of fractures, the lagwire may be placed through an entire limb to, for example, attach an external fixation device to the limb as shown in exemplary FIG. 4E. Other embodiments of bone plates and related adapters are disclosed in U.S. application Ser. No. 12/104,658, filed on Apr. 17, 2008 and entitled "ADJUSTABLE BONE PLATE FIXATION SYSTEM AND METHOD," U.S. application Ser. No. 12/258,013, filed on Oct. 24, 2008 and entitled "BONE SCREW SYSTEM AND METHOD," and U.S. application Ser. No. 12/369,589, filed on Feb. 11, 2009 and entitled "STABILIZATION SYSTEM AND METHOD FOR THE FIXATION OF BONE FRACTURES," which are herein incorporated by reference in their entirety.

Figure 4H:
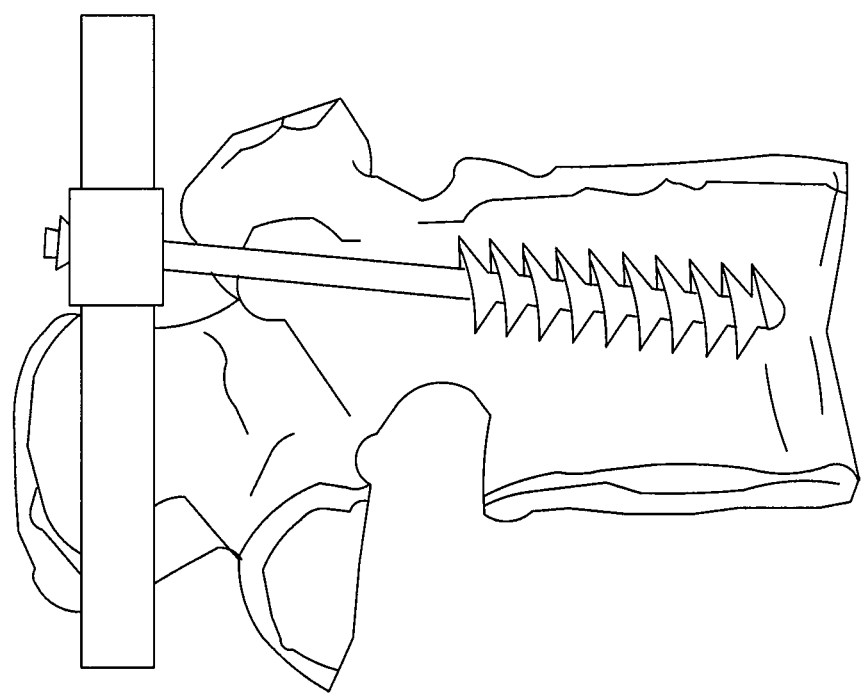
FIG. 4H is a fixation of a spinal injury in accordance with an exemplary embodiment.

FIG. 4H shows a fixation of a vertebrae in accordance with an exemplary embodiment.

The screw is inserted into the vertebrae, then a cap is fitted onto the end of the wire. The cap is specially constructed such that the cap attaches to a rod. The rod may extend along various vertebrae such that the lagwires may extend from various vertebrae and all connect to the same rod. Another screw and lagwire may be inserted into the other side of the vertebrae such that the wire extends from the other side of the vertebrae and its cap connects to a second rod on the other side of the vertebrae for additional stability.

As described herein, the system and method provides a device which is self-drilling, self-tapping and can be inserted under power. The invention also facilitates reducing and fixing fractures in one step. As such, the invention substantially expedites the process for fixation of bone fractures which is, of course, critical during trauma situations in order to stabilize a patient or to minimize the amount of time the patient is on the operating table or under anesthesia. In contrast to typical prior art screws wherein a gliding hole in the near cortex simply guides the screw, the present invention provides the ability for two sides of cortex bone screw fixation. Moreover, because of the strength of the attachment to the bone, the invention enables sufficient fixation even in poor quality bone material. Furthermore, wherein the prior art systems often require the use of cannulated screws in order to utilize a guidewire for placement, the present invention does not require the use of cannulated screws. Because the lagwire includes a tip 4 which creates a pilot hole, taps the bone for threads and fixes the threads into the bone, the system and method minimizes the possibility of inaccurate placement into the distal cortex or missing the distal hole.

In prior art systems, the physician typically cuts a relatively large opening in the skin in order to locate the bone segments, pull the bone segments into alignment, then place the screw into the bones. In the present invention, the system facilitates the percutaneous technique by allowing the physician to cut a minor incision into the skin for the anchor component, insert the anchor component, then pull the bones together with wire 12 and set the cap, all without large incisions or additional incisions.

Another embodiment for a bone fixation device includes a collapsing bone fixation device which is suitably configured to collapse in association with a fracture collapse to minimize or prevent the device from protruding beyond the bone. In an exemplary embodiment, the bone fixation device also includes an internal (i.e., minimal or no contact with the bone) compressive device 140 to maintain compression across the fracture during fracture collapse (e.g., weight bearing by the patient).

Other embodiments for sleeves, and in particular, for sleeves used in connection with guide tubes, are disclosed in U.S. application Ser. No. 12/163,122, filed on Jun. 27, 2008 and entitled "GUIDE SYSTEM AND METHOD FOR THE FIXATION OF BONE FRACTURES," which is herein incorporated by reference in its entirety.

In other embodiments of systems, methods, and devices discussed herein, the systems, methods, and devices may incorporate various features, components, devices, systems, and/or methods for the fixation of bone fractures as described in U.S. application Ser. No. 12/769,529, filed on Apr. 28, 2010 and entitled "BONE SCREW SYSTEM AND METHOD FOR THE FIXATION OF BONE FRACTURES," which is herein incorporated by reference in its entirety.

The present invention is described herein in connection with the fixation of bone fractures; however, one skilled in the art will appreciate that the lagwire system and method described herein may also be used for changing, maintaining, reducing or expanding the distance between objects, object portions, or surfaces, compressing objects or object portions together, or providing pressure to surfaces. For example, the present invention may be used to repair wood products, tree limb damage, breaks in supports or columns, cracks in sculptures or buildings, fractures in sections of concrete or other building materials, cracks or breaks in car parts and/or the like.

In the foregoing specification, the invention has been described with reference to specific embodiments. Various modifications and changes can be made, however, without departing from the scope as set forth in the claims below. The specification and figures are to be regarded in an illustrative manner, rather than a restrictive one, and all such modifications are intended to be included within the scope of present invention. Accordingly, the scope of the invention should be determined by the appended claims and their legal equivalents, rather than by the examples given above. For example, the steps recited in any of the method or process claims may be executed in any order and are not limited to the order presented in the claims.

Benefits, other advantages, and solutions to problems have been described herein with regard to specific embodiments. However, the benefits, advantages, solutions to problems, and any elements that may cause any benefit, advantage, or solution to occur or become more pronounced are not to be construed as critical, required, or essential features or elements of the invention. The scope of the invention is accordingly to be limited by nothing other than the appended claims, in which reference to an element in the singular is not intended to mean "one and only one" unless explicitly so stated, but rather "one or more." Moreover, where a phrase similar to 'at least one of A, B, and C' is used in the claims, it is intended that the phrase be interpreted to mean that A alone may be present in an embodiment, B alone may be present in an embodiment, C alone may be present in an embodiment, or that any combination of the elements A, B and C may be present in a single embodiment; for example, A and B, A and C, B and C, or A and B and C. All structural, chemical, and functional equivalents to the elements of the above-described exemplary embodiments that are known to those of ordinary skill in the art are expressly incorporated herein by reference and are intended to be encompassed by the present claims. Further, a list of elements does not include only those elements but may include other elements not expressly listed or inherent to such process, method, article, or apparatus.

We claim:

1. A method for treating a fracture of a bone, said method comprising:
   inserting a lagwire system into said bone,
      wherein said lagwire system comprises an anchor and a wire;
      wherein said wire has a first end and a second end,
      wherein said anchor is attached to said first end of said wire,
      wherein said anchor includes anchor threads;
      wherein a cap is attached to said second end of said wire;
   cutting said second end of said wire to a particular length;
   fixedly attaching said anchor to a first bone portion;
   sliding a flexible sleeve longitudinally over said wire such that said wire is reciprocally received by said flexible sleeve, after said anchor is fixedly attached to said first bone portion,
      wherein said flexible sleeve has a first sleeve end and a second sleeve end,
   inserting said flexible sleeve into a bone canal that spans across said fracture between said first bone portion and a second bone portion;
   cutting said flexible sleeve to a particular length, after said anchor is fixedly attached to said first bone portion;
      wherein said flexible sleeve is comprised of an interwoven first coiled fiber and second coiled fiber,
      wherein said flexible sleeve is configured to bend while inside said bone canal in any radial direction relative to its centerline into a curved configuration,
      wherein said first coiled fiber includes a plurality of coils, and wherein said second coiled fiber includes a plurality of coils,
      wherein said first coiled fiber and said second coiled fiber form an outer thread on said sleeve,
   threading said outer thread of said sleeve into at least a portion of said bone canal and providing friction against at least a portion of said bone canal;
   engaging said flexible sleeve to said anchor to fixedly attach said flexible sleeve to said anchor, after said anchor is fixedly attached to a first bone portion;
      wherein said anchor is configured to receive said first sleeve end, such that said anchor threads and said outer threads are contiguous;
      wherein said anchor includes tapered threads behind cutting threads, such that said tapered threads are configured to cut into said first sleeve end to secure said first sleeve end to said anchor; and
      wherein threads on said cap and said outer threads on said second sleeve end are contiguous.

2. An implant device comprising:
   a wire having a first end and a second end,
      wherein said second end of said wire is configured to be cut to a particular length;
   an anchor attached to said first end of said wire,
      wherein said anchor is configured to be fixedly attached to a first bone portion,
      wherein said anchor includes anchor threads;
   a cap attached to said second end of said wire; and
   a flexible sleeve having a first sleeve end and a second sleeve end, wherein said flexible sleeve is configured to slide longitudinally over said wire such that said wire is reciprocally received by said flexible sleeve, after said anchor is fixedly attached to said first bone portion,
      wherein said flexible sleeve is configured to be inserted into a bone canal that spans across a fracture between said first bone portion and a second bone portion,
      wherein said flexible sleeve is configured to be cut to a particular length, after said anchor is fixedly attached to said first bone portion,
      wherein said flexible sleeve is comprised of an interwoven first coiled fiber and second coiled fiber,
      wherein said flexible sleeve is configured to bend while inside said bone canal in any radial direction relative to its centerline into a curved configuration,
      wherein said first coiled fiber includes a plurality of coils, and wherein said second coiled fiber includes a plurality of coils,
      wherein said first coiled fiber and said second coiled fiber form an outer thread on said sleeve,
      wherein said outer thread of said sleeve is configured to be threaded into at least a portion of said bone canal and provide friction against at least a portion of said bone canal,
      wherein said flexible sleeve is configured to engage said anchor to fixedly attach said flexible sleeve to said anchor, after said anchor is fixedly attached to a first bone portion;
      wherein said anchor is configured to receive said first sleeve end, such that said anchor threads and said outer threads are contiguous;
      wherein said anchor includes tapered threads behind cutting threads, such that said tapered threads are configured to cut into said first sleeve end to secure said first sleeve end to said anchor; and
   wherein threads on said cap and said outer threads on said second sleeve end are contiguous.

3. The implant device of claim 2, wherein said anchor includes external anchor threads.

4. The implant device of claim 3, wherein said flexible sleeve at least partially includes at least one of shape memory material, plastic, polyetherketone (PEEK), steel, titanium or titanium alloy.

5. The implant device of claim 4, wherein said flexible sleeve is configured to allow treatment to be delivered through a center of said flexible sleeve, wherein said treatment includes at least one of a medication, an adhesive, an ultrasonic vibration, or a bonding material.

6. The implant device of claim 5, wherein said flexible sleeve abuts said anchor creating contiguous outside threads along said anchor and said flexible sleeve.

7. The implant device of claim 6, wherein said first coiled fiber and said second coiled fiber are interwoven such that the first coiled fiber engages outside said second coiled fiber, wherein each coil of said first coiled fiber functions as a thread and each coil of said second coiled fiber separates each of the coils of said first coiled fiber.

8. The implant device of claim 7, wherein said cap includes internal threads which mate with said external threads of said flexible sleeve, wherein said cap further comprises a threaded external distal portion which mates with said first bone portion as a screw interface, and wherein said cap is configured to receive said flexible sleeve such that said cap is configured to slide distally along a length of said flexible sleeve, wherein said cap is configured to engage said flexible sleeve such that said sleeve is at least partially restricted from moving distally relative to said cap.

9. The implant device of claim 8, wherein said flexible sleeve further comprises a proximal end that is hexagonal in shape and configured to receive a hexagonal driver.

10. The implant device of claim 9, wherein said flexible sleeve is configured to receive a force in a proximal direction and be placed in tension to force said first bone portion towards said second bone portion.

11. The implant device of claim 10, further comprising a third coiled fiber, a fourth coiled fiber, a fifth coiled fiber and a sixth coiled fiber, wherein said first coiled fiber, said third coiled fiber , and said fifth coiled fiber each have the same cross section, and wherein said second coiled fiber, said fourth coiled fiber, and said sixth coiled fiber have the same cross section.

12. The implant device of claim 11, wherein a proximal portion of said bone canal is larger such that said flexible sleeve does not engage said proximal portion of said bone canal.

13. The implant device of claim 12, wherein said flexible sleeve is cannulated.

14. The implant device of claim 13, wherein posts engage said flexible sleeve from a perpendicular direction.

\* \* \* \* \*